(12) United States Patent
Locke et al.

(10) Patent No.: US 11,944,520 B2
(45) Date of Patent: Apr. 2, 2024

(54) SEALING SYSTEMS AND METHODS EMPLOYING A HYBRID SWITCHABLE DRAPE

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: 3M Innovative Properties Company, Saint Paul, MN (US)

( * ) Notice: Subject to any disclaimer, the term of this patent is extended or adjusted under 35 U.S.C. 154(b) by 1031 days.

(21) Appl. No.: 16/746,425

(22) Filed: Jan. 17, 2020

(65) Prior Publication Data

US 2020/0146898 A1 May 14, 2020

Related U.S. Application Data

(63) Continuation of application No. 15/410,991, filed on Jan. 20, 2017, now Pat. No. 10,940,047, which is a
(Continued)

(51) Int. Cl.
*A61F 13/00* (2006.01)
*A61F 13/02* (2006.01)
(Continued)

(52) U.S. Cl.
CPC .. *A61F 13/00068* (2013.01); *A61F 13/00059* (2013.01); *A61F 13/00063* (2013.01);
(Continued)

(58) Field of Classification Search
USPC .......................................................... 128/863
See application file for complete search history.

(56) References Cited

U.S. PATENT DOCUMENTS

| 1,355,846 A | 10/1920 | Rannells |
| 1,944,834 A | 1/1934 | Bennett |

(Continued)

FOREIGN PATENT DOCUMENTS

| AU | 550575 B2 | 3/1986 |
| AU | 745271 B2 | 3/2002 |

(Continued)

OTHER PUBLICATIONS

WO 0185248 A1 NPL document, Clarivate Analytics, Nov. 2001, pp. 1-9.*

(Continued)

*Primary Examiner* — Kim M Lewis

(57) ABSTRACT

Systems, kits, methods of manufacturing, and a sealing member for creating a sealed space are described. The sealing member can include a film layer and a first adhesive layer coupled to the film layer. The sealing member can also include a second adhesive layer coupled to the first adhesive layer. A plurality of apertures may extend through the second adhesive layer. Each aperture can expose at least a portion of the first adhesive layer through the second adhesive layer. A plurality of polymer particles may be disposed in the first adhesive layer. The polymer particles can be configured to dissolve in response to interaction with a switching solution.

20 Claims, 13 Drawing Sheets

Related U.S. Application Data continuation-in-part of application No. 14/919,055, filed on Oct. 21, 2015, now Pat. No. 10,265,446, which is a continuation of application No. 13/715,982, filed on Dec. 14, 2012, now Pat. No. 9,192,444, application No. 16/746,425 is a continuation-in-part of application No. 13/715,967, filed on Dec. 14, 2012, now Pat. No. 9,861,532.

(60) Provisional application No. 61/576,774, filed on Dec. 16, 2011, provisional application No. 61/576,786, filed on Dec. 16, 2011.

(51) Int. Cl.
| | | |
|---|---|---|
| *A61F 13/0246* | (2024.01) | |
| *A61M 1/00* | (2006.01) | |
| *B32B 3/26* | (2006.01) | |
| *B32B 27/08* | (2006.01) | |
| *B32B 27/28* | (2006.01) | |
| *B32B 27/30* | (2006.01) | |
| *C09J 7/20* | (2018.01) | |
| *A61B 46/20* | (2016.01) | |

(52) U.S. Cl.
CPC ........ *A61F 13/0216* (2013.01); *A61F 13/023* (2013.01); *A61F 13/0253* (2013.01); *A61F 13/0256* (2013.01); *A61M 1/915* (2021.05); *B32B 3/266* (2013.01); *B32B 27/08* (2013.01); *B32B 27/283* (2013.01); *B32B 27/308* (2013.01); *C09J 7/20* (2018.01); *A61B 2046/205* (2016.02); *A61F 2013/00289* (2013.01); *A61M 1/962* (2021.05); *B32B 2250/24* (2013.01); *B32B 2255/10* (2013.01); *B32B 2307/7242* (2013.01); *B32B 2535/00* (2013.01); *C09J 2301/18* (2020.08); *C09J 2301/208* (2020.08); *Y10T 156/1056* (2015.01)

(56) References Cited

U.S. PATENT DOCUMENTS

| | | |
|---|---|---|
| 2,399,545 A | 4/1946 | Davis |
| 2,547,758 A | 4/1951 | Keeling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,122,140 A | 2/1964 | Crowe, Jr. |
| 3,172,808 A | 3/1965 | Baumann et al. |
| 3,183,116 A | 5/1965 | Schaar |
| 3,214,502 A | 10/1965 | Schaar |
| 3,367,332 A | 2/1968 | Groves |
| 3,376,868 A | 4/1968 | Mondiadis |
| 3,515,270 A | 6/1970 | Yang et al. |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,762,415 A | 10/1973 | Morrison |
| 3,774,611 A | 11/1973 | Tussey et al. |
| 3,777,016 A | 12/1973 | Gilbert |
| 3,779,243 A | 12/1973 | Tussey et al. |
| 3,811,438 A | 5/1974 | Economou |
| 3,826,254 A | 7/1974 | Mellor |
| 3,852,823 A | 12/1974 | Jones |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,174,664 A | 11/1979 | Arnott et al. |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,323,069 A | 4/1982 | Ahr et al. |
| 4,333,468 A | 6/1982 | Geist |
| 4,343,848 A | 8/1982 | Leonard, Jr. |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielsen |
| 4,617,021 A | 10/1986 | Leuprecht |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,705,543 A | 11/1987 | Kertzman |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,773,408 A | 9/1988 | Cilento et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,842,594 A | 6/1989 | Ness |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,935,005 A | 6/1990 | Haines |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Ang et al. |
| 4,996,128 A | 2/1991 | Aldecoa et al. |
| 5,004,502 A | 4/1991 | Ramzan |

(56) References Cited

U.S. PATENT DOCUMENTS

| | | |
|---|---|---|
| 5,010,883 A | 4/1991 | Rawlings et al. |
| 5,018,515 A | 5/1991 | Gilman |
| 5,025,783 A | 6/1991 | Lamb |
| 5,028,597 A | 7/1991 | Kodama et al. |
| 5,037,397 A | 8/1991 | Kalt et al. |
| 5,042,500 A | 8/1991 | Norlien et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,127,601 A | 7/1992 | Schroeder |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,244,457 A | 9/1993 | Karami et al. |
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,271,987 A | 12/1993 | Iskra |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,352,516 A | 10/1994 | Therriault et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,611,373 A | 3/1997 | Ashcraft |
| 5,628,724 A | 5/1997 | DeBusk et al. |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,830,201 A | 11/1998 | George et al. |
| 5,848,966 A | 12/1998 | Gusakov et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,083,616 A | 7/2000 | Dressler |
| 6,086,995 A | 7/2000 | Smith |
| 6,135,116 A | 10/2000 | Vogel et al. |
| 6,159,877 A | 12/2000 | Scholz et al. |
| 6,174,306 B1 | 1/2001 | Fleischmann |
| 6,191,335 B1 | 2/2001 | Robinson |
| 6,201,164 B1 | 3/2001 | Wulff et al. |
| 6,228,485 B1 | 5/2001 | Leiter |
| 6,238,762 B1 | 5/2001 | Friedland et al. |
| 6,241,747 B1 | 6/2001 | Ruff |
| 6,242,665 B1 | 6/2001 | Malowaniec |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,457,200 B1 | 10/2002 | Tanaka et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,806,214 B2 | 10/2004 | Li et al. |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Byordi et al. |
| 7,070,584 B2 | 7/2006 | Johnson et al. |
| 7,154,017 B2 | 12/2006 | Sigurjonsson et al. |
| 7,396,976 B2 | 7/2008 | Hurwitz et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,920,830 B2 | 12/2014 | Mathies |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,861,532 B2 * | 1/2018 | Locke .................. A61F 13/025 |
| 9,877,873 B2 | 1/2018 | Coulthard et al. |
| 9,956,120 B2 | 5/2018 | Locke |
| 10,265,446 B2 * | 4/2019 | Locke ............... A61F 13/00068 |
| 10,940,047 B2 * | 3/2021 | Locke ................ A61F 13/0253 |
| 11,096,830 B2 | 8/2021 | Pratt et al. |
| 2001/0030304 A1 | 10/2001 | Kohda et al. |

(56) References Cited

U.S. PATENT DOCUMENTS

| | | |
|---|---|---|
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0164446 A1 | 11/2002 | Zhou et al. |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0070680 A1 | 4/2003 | Smith et al. |
| 2003/0109855 A1 | 6/2003 | Solem et al. |
| 2003/0158577 A1 | 8/2003 | Ginn et al. |
| 2003/0208175 A1 | 11/2003 | Gross et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0082897 A1 | 4/2004 | Rangel et al. |
| 2004/0082925 A1 | 4/2004 | Patel |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0163278 A1 | 8/2004 | Caspers et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2004/0241214 A1 | 12/2004 | Kirkwood et al. |
| 2005/0034731 A1 | 2/2005 | Rousseau et al. |
| 2005/0054998 A1 | 3/2005 | Poccia et al. |
| 2005/0058810 A1 | 3/2005 | Dodge et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0158442 A1 | 7/2005 | Westermann et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2005/0283105 A1 | 12/2005 | Heaton et al. |
| 2006/0014030 A1 | 1/2006 | Langen et al. |
| 2006/0020235 A1 | 1/2006 | Siniaguine |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0028526 A1 | 2/2007 | Woo et al. |
| 2007/0078366 A1 | 4/2007 | Haggstrom et al. |
| 2007/0135787 A1 | 6/2007 | Raidel et al. |
| 2007/0161937 A1 | 7/2007 | Aali |
| 2007/0185426 A1 | 8/2007 | Ambrosio et al. |
| 2007/0190281 A1 | 8/2007 | Hooft |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2007/0283962 A1 | 12/2007 | Doshi et al. |
| 2008/0009812 A1 | 1/2008 | Riesinger |
| 2008/0027366 A1 | 1/2008 | Da Silva Macedo |
| 2008/0082059 A1 | 4/2008 | Fink et al. |
| 2008/0090085 A1 | 4/2008 | Kawate et al. |
| 2008/0095979 A1 | 4/2008 | Hatanaka et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0062713 A1 | 3/2009 | Nash |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0264807 A1 | 10/2009 | Haggstrom et al. |
| 2009/0292264 A1 | 11/2009 | Hudspeth et al. |
| 2009/0299251 A1 | 12/2009 | Buan |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0030170 A1 | 2/2010 | Keller et al. |
| 2010/0030178 A1 | 2/2010 | MacMeccan et al. |
| 2010/0063467 A1 | 3/2010 | Addison et al. |
| 2010/0069863 A1 | 3/2010 | Olson |
| 2010/0106106 A1 | 4/2010 | Heaton et al. |
| 2010/0106118 A1 | 4/2010 | Heaton et al. |
| 2010/0111919 A1 | 5/2010 | Abuzaina et al. |
| 2010/0125259 A1 | 5/2010 | Olson |
| 2010/0159192 A1 | 6/2010 | Cotton |
| 2010/0168633 A1 | 7/2010 | Bougherara et al. |
| 2010/0168635 A1 | 7/2010 | Freiding et al. |
| 2010/0185163 A1 | 7/2010 | Heagle |
| 2010/0191197 A1 | 7/2010 | Braga et al. |
| 2010/0212768 A1 | 8/2010 | Resendes |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0272784 A1 | 10/2010 | Kantner |
| 2010/0286582 A1 | 11/2010 | Simpson et al. |
| 2010/0305490 A1 | 12/2010 | Coulthard et al. |
| 2010/0305524 A1 | 12/2010 | Vess et al. |
| 2010/0312159 A1 | 12/2010 | Aali et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0054423 A1 | 3/2011 | Blott et al. |
| 2011/0112457 A1 | 5/2011 | Holm et al. |
| 2011/0118683 A1 | 5/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1 | 9/2011 | Simmons et al. |
| 2011/0229688 A1 | 9/2011 | Cotton |

(56) References Cited

U.S. PATENT DOCUMENTS

| | | |
|---|---|---|
| 2011/0237969 A1 | 9/2011 | Eckerbom et al. |
| 2011/0244010 A1 | 10/2011 | Doshi |
| 2011/0257612 A1 | 10/2011 | Locke et al. |
| 2011/0257617 A1 | 10/2011 | Franklin |
| 2011/0280926 A1 | 11/2011 | Junginger |
| 2011/0281084 A1 | 11/2011 | Ashwell |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0109034 A1 | 5/2012 | Locke et al. |
| 2012/0123220 A1 | 5/2012 | Iyer et al. |
| 2012/0123359 A1 | 5/2012 | Reed |
| 2012/0143157 A1 | 6/2012 | Riesinger |
| 2012/0237722 A1 | 9/2012 | Seyler et al. |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0098360 A1 | 4/2013 | Hurmez et al. |
| 2013/0116661 A1 | 5/2013 | Coward et al. |
| 2013/0150763 A1 | 6/2013 | Mirzaei et al. |
| 2013/0152945 A1 | 6/2013 | Locke et al. |
| 2013/0165887 A1 | 6/2013 | Eric Mitchell et al. |
| 2013/0172843 A1 | 7/2013 | Kurata |
| 2013/0189339 A1 | 7/2013 | Vachon |
| 2013/0261585 A1 | 10/2013 | Lee |
| 2013/0296760 A1 | 11/2013 | Ramminger et al. |
| 2013/0304007 A1 | 11/2013 | Toth |
| 2013/0330486 A1 | 12/2013 | Shields |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1 | 6/2014 | Patel |
| 2014/0249495 A1 | 9/2014 | Mumby et al. |
| 2014/0309574 A1 | 10/2014 | Cotton |
| 2014/0336557 A1 | 11/2014 | Durdag et al. |
| 2014/0350494 A1 | 11/2014 | Hartwell et al. |
| 2014/0352073 A1 | 12/2014 | Goenka |
| 2015/0030848 A1 | 1/2015 | Goubard |
| 2015/0045752 A1 | 2/2015 | Grillitsch et al. |
| 2015/0057625 A1 | 2/2015 | Coulthard |
| 2015/0080788 A1 | 3/2015 | Blott et al. |
| 2015/0080815 A1 | 3/2015 | Chakravarthy et al. |
| 2015/0094646 A1 | 4/2015 | Vinton |
| 2015/0119830 A1 | 4/2015 | Luckemeyer et al. |
| 2015/0119833 A1 | 4/2015 | Coulthard et al. |
| 2015/0119834 A1 | 4/2015 | Locke et al. |
| 2015/0141941 A1 | 5/2015 | Allen et al. |
| 2015/0190286 A1 | 7/2015 | Allen et al. |
| 2015/0209200 A1 | 7/2015 | Fouillet et al. |
| 2015/0217077 A1 | 8/2015 | Scampoli et al. |
| 2015/0290041 A1 | 10/2015 | Richard |
| 2016/0000610 A1 | 1/2016 | Riesinger |
| 2016/0067107 A1 | 3/2016 | Cotton |
| 2016/0144084 A1 | 5/2016 | Collinson et al. |

FOREIGN PATENT DOCUMENTS

| | | | |
|---|---|---|---|
| AU | 755496 B2 | 12/2002 | |
| AU | 2009200608 A1 | 10/2009 | |
| CA | 2005436 A1 | 6/1990 | |
| CN | 87101823 A | 8/1988 | |
| DE | 26 40 413 A1 | 3/1978 | |
| DE | 9104308 U1 | 8/1991 | |
| DE | 43 06 478 A1 | 9/1994 | |
| DE | 29 504 378 U1 | 9/1995 | |
| DE | 202004018245 U1 | 7/2005 | |
| DE | 202014100383 U1 | 2/2015 | |
| EP | 0097517 A1 | 1/1984 | |
| EP | 0100148 A1 | 2/1984 | |
| EP | 0117632 A2 | 9/1984 | |
| EP | 0161865 A2 | 11/1985 | |
| EP | 0251810 A2 | 1/1988 | |
| EP | 0275353 A2 | 7/1988 | |
| EP | 0358302 A2 | 3/1990 | |
| EP | 0538917 A1 | 4/1993 | |
| EP | 0630629 A1 | 12/1994 | |
| EP | 0659390 A2 | 6/1995 | |
| EP | 0633758 B1 | 10/1996 | |
| EP | 1002846 A1 | 5/2000 | |
| EP | 1018967 A1 | 7/2000 | |
| EP | 2578193 A1 | 4/2013 | |
| GB | 692578 A | 6/1953 | |
| GB | 1386800 A | 3/1975 | |
| GB | 2195255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2377939 A | 1/2003 | |
| GB | 2392836 A | 3/2004 | |
| GB | 2393655 A | 4/2004 | |
| GB | 2425487 A | 11/2006 | |
| GB | 2452720 A | 3/2009 | |
| GB | 2496310 A | 5/2013 | |
| JP | 1961003393 | 2/1961 | |
| JP | S62139523 U | 9/1987 | |
| JP | S62-275456 A | 11/1987 | |
| JP | H0190516 U | 6/1989 | |
| JP | H02139626 U | 11/1990 | |
| JP | 2002238944 A | 8/2002 | |
| JP | 2004073483 A | 3/2004 | |
| JP | 2005205120 A | 8/2005 | |
| JP | 2005-304877 A | 11/2005 | |
| JP | 2007254515 A | 10/2007 | |
| JP | 4129536 B2 | 8/2008 | |
| JP | 2012050274 A | 3/2012 | |
| SG | 71559 | 4/2002 | |
| WO | 80/02182 A1 | 10/1980 | |
| WO | 87/04626 A1 | 8/1987 | |
| WO | 8707164 A1 | 12/1987 | |
| WO | 90/010424 A1 | 9/1990 | |
| WO | 93/009727 A1 | 5/1993 | |
| WO | 94/20041 A1 | 9/1994 | |
| WO | 96/05873 A1 | 2/1996 | |
| WO | 9622753 A1 | 8/1996 | |
| WO | 97/18007 A1 | 5/1997 | |
| WO | 99/13793 A1 | 3/1999 | |
| WO | 99/65542 A1 | 12/1999 | |
| WO | 01/36258 A1 | 5/2001 | |
| WO | 01/60296 A1 | 8/2001 | |
| WO | 0168021 A1 | 9/2001 | |
| WO | 0185248 A1 | 11/2001 | |
| WO | 0190465 A2 | 11/2001 | |
| WO | WO-0185249 A1 * | 11/2001 | ............ A61L 29/14 |
| WO | 0243743 A1 | 6/2002 | |
| WO | 02062403 A1 | 8/2002 | |
| WO | 03-018098 A2 | 3/2003 | |
| WO | 03045294 A1 | 6/2003 | |
| WO | 03045492 A1 | 6/2003 | |
| WO | 03053484 A1 | 7/2003 | |
| WO | 2004024197 A1 | 3/2004 | |
| WO | 2004037334 A1 | 5/2004 | |
| WO | 2004112852 A1 | 12/2004 | |
| WO | 2005002483 A2 | 1/2005 | |
| WO | 2005062896 A2 | 7/2005 | |
| WO | 2005105176 A1 | 11/2005 | |
| WO | 2005123170 A1 | 12/2005 | |
| WO | 2007022097 A2 | 2/2007 | |
| WO | 2007030601 A2 | 3/2007 | |
| WO | 2007070269 A1 | 6/2007 | |

(56) References Cited

FOREIGN PATENT DOCUMENTS

| | | |
|---|---|---|
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008/041926 A1 | 4/2008 |
| WO | 2008048527 A2 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2008149107 A1 | 12/2008 |
| WO | 2009002260 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009124100 A1 | 10/2009 |
| WO | 2009126103 A1 | 10/2009 |
| WO | 2010011148 A1 | 1/2010 |
| WO | 2010016791 A1 | 2/2010 |
| WO | 2010032728 A1 | 3/2010 |
| WO | 2010056977 A2 | 5/2010 |
| WO | 2010129299 A2 | 11/2010 |
| WO | 2011008497 A2 | 1/2011 |
| WO | 2011026498 A1 | 3/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011135284 A1 | 11/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013066426 A2 | 5/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014097069 A1 | 6/2014 |
| WO | 2014113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

Australian Office Action for related application 2018278874, dated Feb. 12, 2020.
Japanese Office Action for related application 2017-182858, dated Mar. 31, 2020.
Office Action for related U.S. Appl. No. 14/630,290, dated Apr. 30, 2020.
Office Action for related U.S. Appl. No. 15/793,044, dated May 13, 2020.
EP Informal Search Report for related application 19186600.3.
Office Action for related U.S. Appl. No. 15/884,198, dated May 19, 2020.
Office Action for related U.S. Appl. No. 16/151,005, dated Apr. 13, 2021.
European Office Action for related application 12812464.1, dated Jun. 4, 2021.
Office Action for related U.S. Appl. No. 16/287,862, dated Nov. 2, 2021.
Office Action for related U.S. Appl. No. 16/577,535, dated Mar. 15, 2022.
Office Action for related U.S. Appl. No. 16/513,481, dated Mar. 30, 2022.
Office Action for related U.S. Appl. No. 16/528,441, dated May 9, 2022.
Extended European Search Report for related application 21209807.3, dated Jun. 1, 2022.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.

(56) References Cited

OTHER PUBLICATIONS

Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Office Action for related U.S. Appl. No. 17/009,328, dated Oct. 14, 2022.
Office Action for related U.S. Appl. No. 16/733,023, dated Feb. 9, 2023.
Office Action for related U.S. Appl. No. 17/122,855, dated Feb. 7, 2023.
Office Action for related U.S. Appl. No. 16/513,481, dated Feb. 22, 2023.
Office Action for related U.S. Appl. No. 17/151,489, dated Feb. 23, 2023.
Office Action for related U.S. Appl. No. 17/374,467, dated Apr. 5, 2023.
International Search Report and Written Opinion date dated Oct. 19, 2010; PCT International Application No. PCT/US2009/036217.
NPD 1000 Negative Pressure Would Therapy System, Kalypto Medical, pp. 1-4, dated Sep. 2008.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
International Search Report and Written opinion for PCT Application PCT/US2009/036222, dated Dec. 15, 2009.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
Extended European Search Report for corresponding Application No. 15194949.2, dated Mar. 11, 2016.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion for PCT International Application No. PCT/US2011/028344, dated Jun. 1, 2011.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).

(56) References Cited

OTHER PUBLICATIONS

European Search Report for corresponding application 17183683.6, dated Sep. 18, 2017.
European Search Report for corresponding application 17164033.7, dated Oct. 13, 2017.
Office Action for corresponding U.S. Appl. No. 14/919,055, dated Jun. 2, 2017.
Extended European Search Report for corresponding application 17191970.7, dated Oct. 26, 2017.
Japanese office action for related application 2015-547246, dated Sep. 5, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related application PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
Office Action for related U.S. Appl. No. 14/919,055, dated Jan. 23, 2018.
Extended European Search Report for related application 17177013.4, dated Mar. 19, 2018.
Extended European Search Report for related application 16793298.7, dated Mar. 27, 2018.
Japanese Notice of Rejection in corresponding application 2017-182858, dated Aug. 21, 2018.
Office Action for related U.S. Appl. No. 14/965,675, dated Aug. 9, 2018.
Office Action for related U.S. Appl. No. 15/307,472, dated Oct. 18, 2018.
Office Action for related U.S. Appl. No. 14/965,675, dated Dec. 12, 2018.
Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 14/080,348, dated Apr. 12, 2019.
Japanese Notice of Rejection for related application 2016-570333, dated Feb. 26, 2019.
Office Action for related U.S. Appl. No. 15/410,991, dated May 2, 2019.
Office Action for related U.S. Appl. No. 15/314,426, dated Aug. 29, 2019.
Office Action for related U.S. Appl. No. 15/600,451, dated Nov. 27, 2019.
Office Action for related U.S. Appl. No. 16/007,060, dated Aug. 18, 2020.
Office Action for related U.S. Appl. No. 15/937,485, dated Aug. 4, 2020.
Office Action for related U.S. Appl. No. 15/793,044, dated Sep. 24, 2020.
Extended European Search Report for related application 20185730.7, dated Oct. 9, 2020.
Japanese Office Action for related application 2017-182858, dated Sep. 15, 2020.
Office Action for related U.S. Appl. No. 16/291,721, dated Oct. 28, 2020.
Advisory Action for related U.S. Appl. No. 15/793,044, dated Dec. 9, 2020.
Japanese Office Action for related application 2019-235427, dated Jan. 5, 2021.
Office Action for related U.S. Appl. No. 16/733,023, dated Sep. 7, 2023.
Office Action for related U.S. Appl. No. 17/480,930, dated Oct. 3, 2023.
Office Action for related U.S. Appl. No. 17/226,976, dated Dec. 21, 2023.
European Examination Report for related application 21158749.8, dated Feb. 8, 2024.

\* cited by examiner

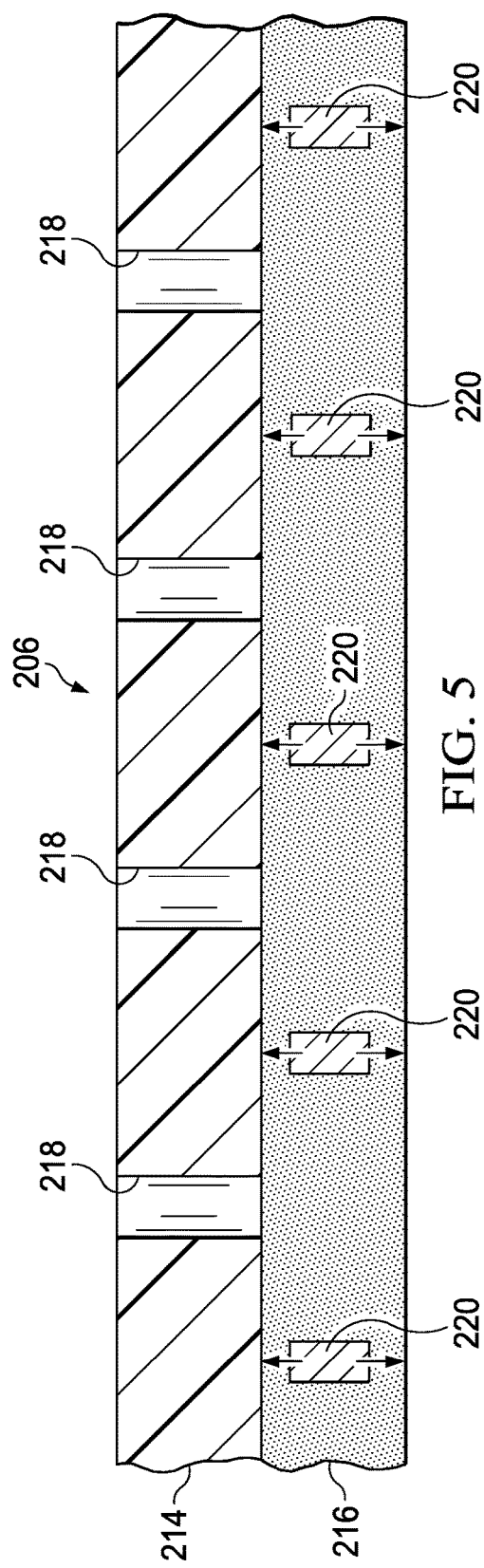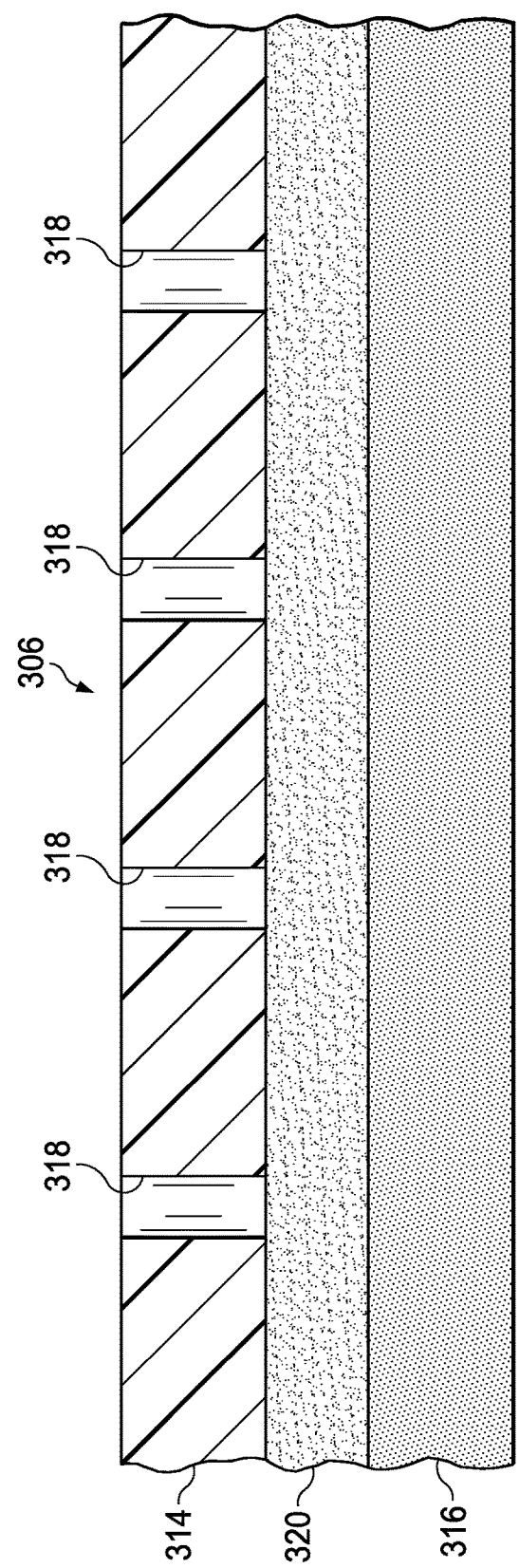

SEALING SYSTEMS AND METHODS EMPLOYING A HYBRID SWITCHABLE DRAPE

CROSS-REFERENCE TO RELATED APPLICATIONS

This application is a continuation of U.S. patent application Ser. No. 15/410,991, filed Jan. 20, 2017, entitled "Sealing Systems and Methods Employing a Hybrid Switchable Drape," which is a continuation-in-part of U.S. patent application Ser. No. 14/919,055, filed Oct. 21, 2015, now U.S. Pat. No. 10,265,446, entitled "Sealing Systems and Methods Employing a Switchable Drape," which is a continuation of U.S. patent application Ser. No. 13/715,982, filed Dec. 14, 2012, now U.S. Pat. No. 9,192,444, entitled "Sealing Systems and Methods Employing a Switchable Drape," which claims priority to U.S. Provisional Patent Application No. 61/576,786, filed Dec. 16, 2011, entitled "Sealing Systems and Methods Employing a Switchable Drape." This application is also a continuation-in-part of U.S. patent application Ser. No. 13/715,967, filed Dec. 14, 2012, now U.S. Pat. No. 9,861,532, entitled "Releasable Medical Drapes," which claims priority to U.S. Provisional Patent Application No. 61/576,774, filed Dec. 16, 2011, entitled "Releasable Medical Drapes." The disclosures of each of the foregoing applications are hereby incorporated by reference in their entirety.

TECHNICAL FIELD

The present disclosure relates generally to medical systems, devices, and methods for treating a patient with negative pressure, and more particularly, but not by way of limitation, to sealing systems and methods employing a switchable drape.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with negative pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for creating a sealed therapeutic environment for treating a tissue site are set forth in the appended claims. Illustrative embodiments are also provided to enable a person skilled in the art to make and use the claimed subject matter.

For example, a sealing member is described. The sealing member can include a film layer and a first adhesive layer coupled to the film layer. The sealing member can also include a second adhesive layer coupled to the first adhesive layer. A plurality of apertures may extend through the second adhesive layer. Each aperture can expose at least a portion of the first adhesive layer through the second adhesive layer. A plurality of polymer particles may be disposed in the first adhesive layer. The polymer particles can be configured to dissolve in response to interaction with a switching solution.

More generally, a system for providing negative-pressure therapy is described. The system can include a tissue interface configured to be disposed proximate to a tissue site and a cover configured to be disposed over the tissue interface to form a sealed space containing the tissue interface. The cover may include a barrier layer, an acrylic adhesive layer coupled to the barrier layer, and a silicone gel layer coupled to the acrylic adhesive layer. A plurality of apertures may extend through the silicone gel layer, exposing at least a portion of the acrylic adhesive layer through the silicone gel layer. A plurality of release agents may be disposed in the acrylic adhesive layer. The release agents can be configured to dissolve in response to interaction with a release solution. The system can also include a negative-pressure source configured to be fluidly coupled to the sealed space to draw fluid from the sealed space.

Alternatively, other example embodiments may describe a method of manufacturing a cover. A polyurethane layer may be provided. A plurality of release agents may be disposed in an acrylic adhesive. A surface of the polyurethane layer may be coated with the acrylic adhesive to form an acrylic adhesive layer. A surface of the acrylic adhesive layer may be coated with a silicone adhesive to form a silicone adhesive layer. A plurality of openings may be formed in the silicone adhesive layer to expose the acrylic adhesive layer through the silicone adhesive layer. The release agents are configured to reduce a bond strength of the acrylic adhesive in response to exposure to a release solution.

A method for removing a drape is also described. A switching solution may be applied to an edge of a drape. The drape may include a film layer; a first adhesive layer coupled to the film layer; and a second adhesive layer coupled to the first adhesive layer. The drape may also include a plurality of apertures extending through the second adhesive layer. Each aperture may expose at least a portion of the first adhesive layer through the second adhesive layer. The drape may also include a plurality of polymer particles disposed in the first adhesive layer. The polymer particles may be dissolved with the switching solution to reduce a bond strength of the first adhesive layer. The edge of the drape can be lifted to remove the drape from a surface.

A kit for forming a seal over a tissue site is also described herein. The kit can include a sealing member configured to be disposed over a tissue interface to form a sealed space containing the tissue interface. The sealing member can include a film layer, a first adhesive layer coupled to the film layer, and a second adhesive layer coupled to the first adhesive layer. A plurality of apertures may extend through the second adhesive layer, exposing at least a portion of the first adhesive layer through the second adhesive layer. A plurality of polymer particles may be disposed in the first adhesive layer. The kit also includes a switching solution. The polymer particles may be configured to dissolve in response to interaction with a switching solution.

Another sealing member is also described. The sealing member can include a film layer and a first adhesive layer coupled to the film layer. The sealing member can also include a second adhesive layer coupled to the first adhesive layer. The second adhesive layer may have a plurality of apertures extending through the second adhesive layer. Each aperture may expose at least a portion of the first adhesive layer through the second adhesive layer. A plurality of polymer particles may be disposed in the first adhesive layer. The polymer particles can be configured to dissolve in response to interaction with a switching solution. A plurality of perforations may extend through the film layer. Each perforation of the plurality of perforations may be registered with a respective aperture of the plurality of apertures.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 5 is a cross-sectional view of another cover that can be used with the system of FIG. 1;

FIG. 6 is a cross-sectional view of another cover that can be used with the system of FIG. 1;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientations assume a frame of reference consistent with or relative to a patient in a position to receive treatment. However, as should be recognized by those skilled in the art, this frame of reference is merely a descriptive expedient rather than a strict prescription.

In the following detailed description of illustrative, non-limiting embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

Figure 1:
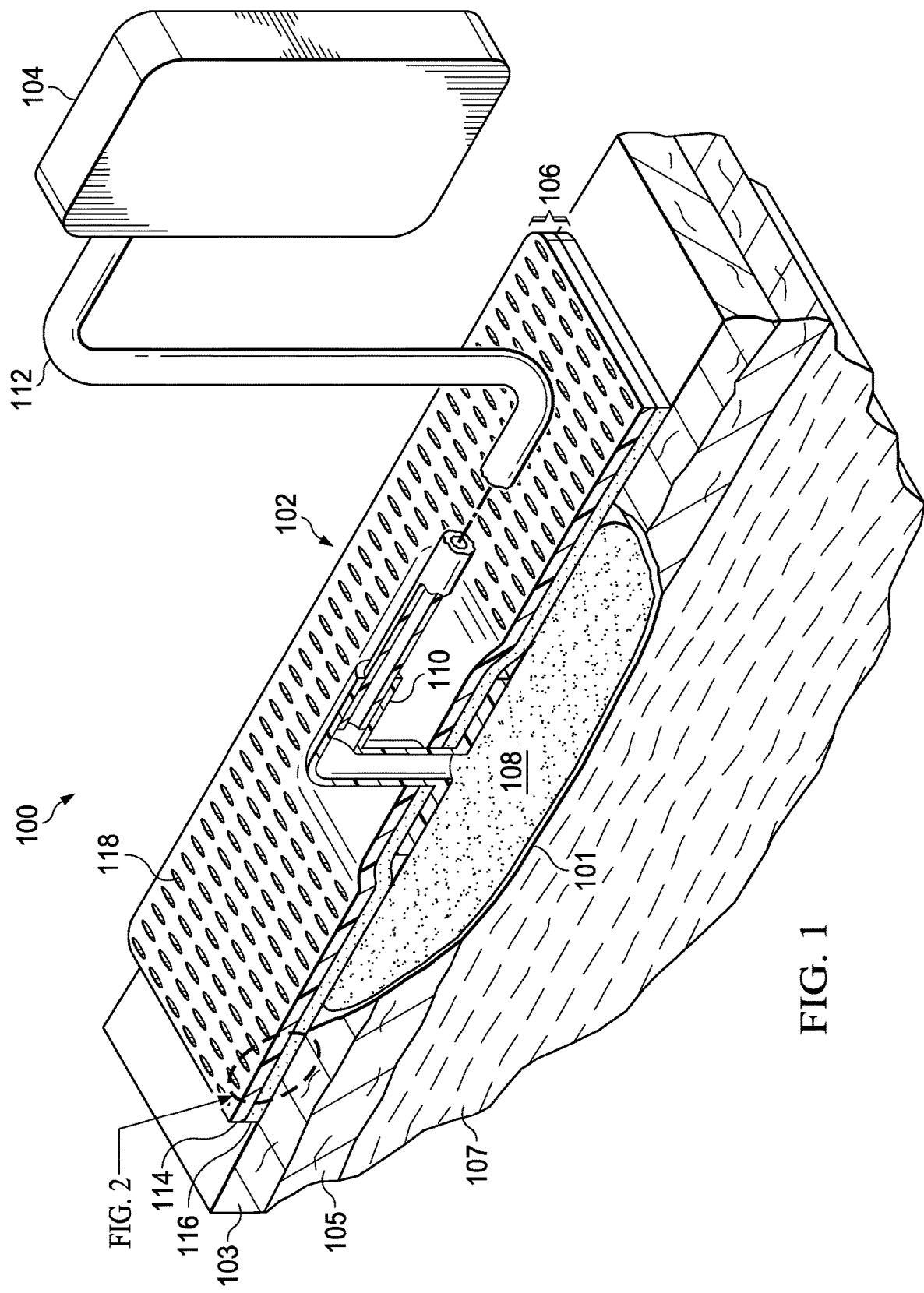
FIG. 1 is a perspective view (with a portion shown in cross section) of an illustrative embodiment of a system for treating a tissue site on a patient that employs an illustrative cover.

FIG. 1 is a sectional view, with a portion shown in elevation, of a therapy system 100 that can provide therapy, such as negative-pressure therapy, to a tissue site 101. The tissue site 101 may be a wound that is through an epidermis 103, a dermis 105, and into a subcutaneous tissue 107, but any wound size, depth, or tissue may be involved.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108. The cover 106 may include an elastomeric film 114 and an attachment device 116. In some embodiments, the dressing 102 may be part of a sealing subsystem that can include the dressing 102 and a switching solution.

In some embodiments, a dressing interface 110 may facilitate coupling the negative-pressure source 104 to the dressing 102. For example, such a dressing interface may be a T.R.A.C.® Pad or Sensa T.R.A.C.® Pad available from KCI of San Antonio, Texas. The therapy system 100 may optionally include a fluid container coupled to the dressing 102 and to the negative-pressure source 104.

Additionally, the therapy system 100 may include sensors to measure operating parameters and provide feedback signals to a controller indicative of the operating parameters. As illustrated in FIG. 1, for example, the therapy system 100 may include a pressure sensor, an electric sensor, or both, coupled to the controller. The pressure sensor may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube 112. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, the tube 112 may mechanically and fluidly couple the dressing 102 to the negative-pressure source 104 in some embodiments. In general, components of the therapy system 100 may be coupled directly or indirectly. For example, the negative-pressure source 104 may be directly coupled to the tube 112, and may be indirectly coupled to the dressing 102 through the tube 112 and the dressing interface 110.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, the negative-pressure source 104 may be combined with a controller and other components into a therapy unit. A negative-pressure supply may also have one or more supply ports configured to facilitate coupling and de-coupling the negative-pressure supply to one or more distribution components. In another illustrative embodiment, a negative-pressure supply may be a micro-pump. A micro-pump may be a pump sized to be coupled to a cover, such as the cover 106.

A controller may be a microprocessor or computer programmed to operate one or more components of the therapy system 100, such as the negative-pressure source 104. In some embodiments, for example, a controller may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. A controller is also preferably configured to receive one or more input signals, such as a feedback signal, and programmed to modify one or more operating parameters based on the input signals.

Sensors are generally known in the art as any apparatus operable to detect or measure a physical phenomenon or property, and generally provide a signal indicative of the phenomenon or property that is detected or measured. For example, a pressure sensor and an electric sensor may be configured to measure one or more operating parameters of the therapy system 100. In some embodiments, a pressure sensor may be a transducer configured to measure pressure in a pneumatic pathway and convert the measurement to a signal indicative of the pressure measured. In some embodiments, for example, a pressure sensor may be a piezoresistive strain gauge. An electric sensor may optionally measure operating parameters of the negative-pressure source 104, such as the voltage or current, in some embodiments. Preferably, the signals from sensors are suitable as input signals to a controller, but some signal conditioning may be appropriate in some embodiments. For example, the signal may need to be filtered or amplified before it can be processed by a controller. Typically, the signal is an electrical signal, but may be represented in other forms, such as an optical signal.

A container is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Texas.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site if pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The provision of negative pressure therapy with negative pressure therapy systems, such as the therapy system 100, is increasingly being performed with smaller therapy devices that use battery power rather than a connection to an electrical outlet. Use of battery power decreases the total power supply available to a therapy device. As a result, power drains that would be considered negligible in a device powered through an electrical outlet connection may significantly reduce the ability of the therapy device to provide therapy. A power drain refers to operation of the therapy device that requires use of electrical power, for example, operation of a pump to generate negative pressure. Power drains may be caused by low-level dressing leaks, for example. A low-level dressing leak can drain power from a battery of a therapy device by repeatedly triggering operation of the therapy device to maintain the necessary negative pressure at the tissue site. These power drains shorten the useful life of the therapy device before disposal of the therapy device, recharge of the battery, or battery replacement is required. Leak detection techniques may help to identify some leaks that may then be sealed by the user; however, low level leaks will challenge the most sensitive leak detection systems and may often go undetected.

Low level dressing leaks may occur between the cover and the epidermis surrounding a tissue site when the cover fails to completely seal to the epidermis. Covers are a balance between the strength of the adhesive required to enable the cover to seal against leaks and the pain which may result when the cover is removed. A bonding adhesive may be better for sealing, but the adhesive strength would cause significantly more discomfort upon cover removal. In addition, removing a cover with a bonding adhesive may cause significant damage to patients having delicate or damaged skin.

A cover that has a sealing adhesive can fill gaps between the drape and the epidermis to limit leaks and can be easy to remove with low discomfort to the patient. Various sealing, gap-filling adhesives, such as silicone, hydrocolloids, and hydrogels, have been tried but each has drawbacks. For example, hydrogel adhesives are usually low tack and prone to swelling, creep, and mobility when used with fluid systems. In another example, silicone adhesives can fill gaps and seal, but are not breathable and may lose the necessary mechanical bonding strength as the silicone adhesives interact with moisture during use. To counter these problems, silicone adhesives often require additional materials to secure the silicone adhesive to the patient. For example, a low leak cover may be formed from two adhesive layers: a thick sealing adhesive, perhaps in the shape of a gasket or ring, and a thinner bonding adhesive layer used to keep the sealing adhesive in place. The thinner bonding adhesive may be applied as cover strips, or combined with the thicker sealing adhesive as an outer border. Low-leak covers constructed in this way can be more complex than a cover using a single adhesive, increasing the complexity of manipulation and operation.

The therapy system 100 can address these problems by providing a cover having a bonding adhesive with a high bond strength, and switchable characteristics. For example, the bonding adhesive may have a plurality of polymer particles disposed in the bonding adhesive. If the cover is to be removed, a switching solution can be applied to the cover to dissolve the polymer particles, causing the bonding adhesive to decrease in bond strength. In this manner, the cover can provide a seal against a tissue site that may be highly exudating or in a difficult to seal area, without causing additional trauma to the tissue site. The therapy system 100 can also address these problems by providing a cover having a bonding adhesive with a high bond strength paired with a sealing adhesive having good sealing characteristics. In some embodiments, the bonding adhesive can also be switchable, permitting the bonding adhesive to have a first bond strength during use of the cover that can be transitioned to a second bond strength if the cover is to be removed.

In some embodiments, the cover 106 may provide a bacterial barrier and protection from physical trauma. The cover 106 can be used as a component of the dressing 102 during the provision of negative-pressure therapy and as a component of the dressing 102 without the provision of negative-pressure therapy. The cover 106 may also be constructed from a material that can reduce evaporative losses and provide a fluid seal between two components or two environments, such as between a therapeutic environment and a local external environment. The cover 106 may be a film layer or barrier layer, such as the elastomeric film 114, or a membrane that can provide a seal adequate to maintain a negative pressure at a tissue site for a given negative-pressure source. Elastomeric material generally refers to a polymeric material that has rubber-like properties. More specifically, most elastomers have ultimate elongations greater than 100% and a significant amount of resilience. The resilience of a material refers to the ability of the material to recover from an elastic deformation. Examples of elastomers include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Examples of the elastomeric film 114 can include a silicone drape, a 3M Tegaderm® drape, or a polyurethane (PU) drape such as one available from Avery Dennison Corporation of Pasadena, California.

The cover 106 may have a high moisture-vapor transmission rate (MVTR). MVTR represents the amount of moisture that can pass through a material in a given period of time. For example, the cover 106 may have an MVTR greater than about 300 $g/m^2/24$ hours or, more typically, greater than about 1000 $g/m^2/24$ hours or more. In some example embodiments, the elastomeric film 114 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

Additional examples of suitable examples of the elastomeric film 114 include one or more of the following: hydrophilic polyurethanes, cellulosics, hydrophilic polyamides, polyvinyl alcohol, polyvinyl pyrrolidone, hydrophilic silicone polymers, hydrophilic acrylics, hydrophilic silicone elastomers and copolymers of these. As one specific, illustrative, non-limiting embodiment, the elastomeric film 114 may be a breathable cast mat polyurethane film sold under the name INSPIRE 2301 from Exopack Advanced Coatings of Wrexham, United Kingdom, having an MVTR (inverted cup technique) of 14500-14600 $g/m^2/24$ hours. The elastomeric film 114 may have various thicknesses, such as about 10 microns to about 100 microns (μm), e.g., 15, 20, 30, 40, 50, 60, 70, 80, 90, 100 microns or any number in the stated range.

The attachment device 116 may be used to attach the cover 106 to an attachment surface, such as undamaged epidermis, a gasket, or another cover. The attachment device 116 may take many forms. For example, an attachment device may be a medically-acceptable, pressure-sensitive adhesive that extends about a periphery, a portion, or an entire sealing member. In some embodiments, the attachment device 116 may be an acrylic adhesive having a coating weight between 25-65 grams per square meter (gsm) that can be coated onto some or all of the elastomeric film 114. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The attachment device 116 may have a bond strength one to two times stronger than adhesives used on most covers. For example, without limitation, one cover, for example, MED1827A by Avery, has a bond strength of about 1.44N/ cm to a polythene substrate using a 90 degree angle test according to American Society for Testing and Materials ("ASTM") standard ASTM D3330. Whereas, according to one illustrative embodiment, the cover 106 may have a bond strength in the range of greater than about 1.44N/cm to about 2.88N/cm under similar testing conditions. The attachment device 116 typically has a thickness in the range of about 0.3 mm to about 1.5 mm. The attachment device 116 may be formed from an acrylic adhesive or another adhesive. The attachment device 116 can be considered flowable, permitting the attachment device 116 to fill any cracks or crevices in the epidermis 103 adjacent the tissue site 101 to form a strong fluid seal and maintain that seal when negative pressure is applied to the sealed space. An adhesive that is flowable may readily move into small surface contours, such as grooves on a surface of the epidermis or an edge of a cover. Adhesives that flow and provide close contact between objects and form a fluid-tight seal. In some embodiments, an adhesive that is flowable may have a value between about 20 mm and about 25 mm in a cone penetration test conducted using a 60 second dwell time and a 62.5 g cone according to International Organization for Standardization (ISO) DIN ISO 2137.

The attachment device 116 may be switchable. For example, the attachment device 116 may have a first bond strength and, after application of an external stimulus, a second bond strength. For example, the attachment device 116 may have the first bond strength, but after interaction with or exposure to a switching solution, the attachment device 116 may have a second bond strength. In some embodiments, interaction with the switching solution may reduce the bond strength of the attachment device 116 so that the second bond strength is less than the first bond strength.

The switching solution may be a release solution formed from one or more of the following: alcohols, such as ethanol, methanol, propyl alcohols, such as isopropyl alcohol, isopropanol, and other alcohols such as butanols, esters such as butyl ethanoate (acetate), ketones, such as propanone (acetone), natural oils such as linseed, soyer, blends of all these materials with each other, and may also be blended with water. In some embodiments, the switching solution may be a mixture of water and a weak acid or a mixture of water and one or more of ethanol and isopropanol. The switching solution may contain additional components such as a local pain killer or analgesic, for example, lidocaine, prilocaine, bupivacaine, or mixtures of these, or another suitable substance. The switching solution may be kept in a bottle, vial, pouch, sealed wipe, or other convenient storage or delivery means.

The switching solution can reduce the bond strength of the attachment device 116 from the first bond strength to the second bond strength. For example, if the attachment device 116 has an initial bond strength of $A_1$, after application of the switching solution, the attachment device 116 may have a bond strength, $A_2$. In some embodiments, the bond strength $A_2$ is less than the bond strength $A_1$, for example, $A_2<A_1$. The bond strength $A_2$ after application of the switching solution may be less than about 70% of the original bond strength, 70% $A_1$, or even less, for example, 60% $A_1$, 50% $A_1$, 40 $A_1$, 30% $A_1$, 20% $A_1$, 10% $A_1$, or 0% $A_1$. Many permutations are possible, but in one embodiment, the cover 106 has twice the bond strength of a traditional drape, but at removal has only half or less than half of the bond strength of a traditional drape.

Figure 2:
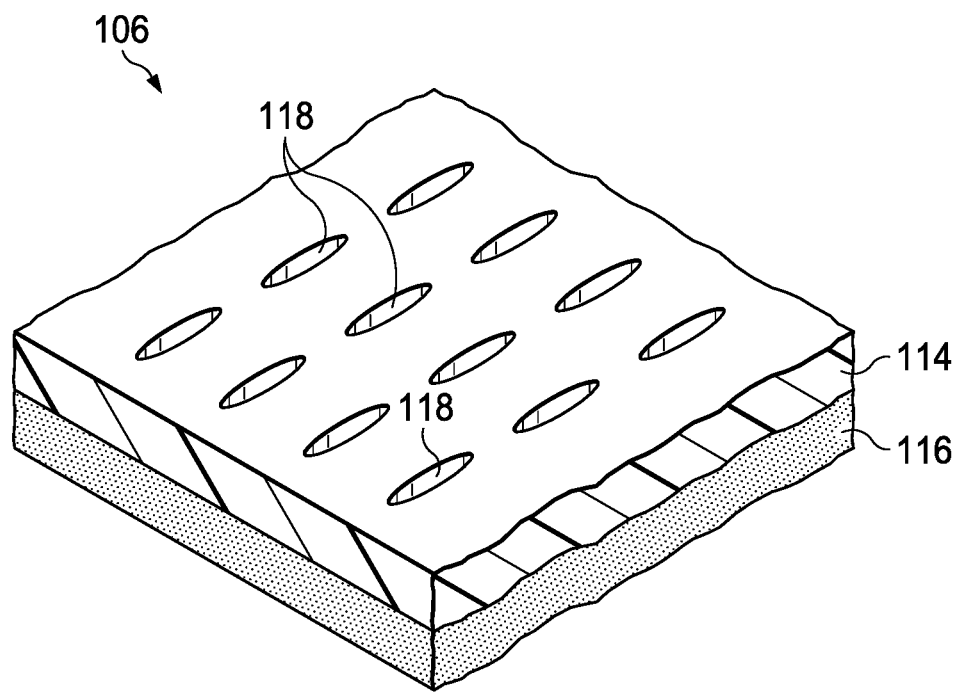
FIG. 2 is a perspective view (with a portion shown in cross section) of a portion of the illustrative cover of FIG. 1.

FIG. 2 is a perspective view (with a portion shown in cross section) of a portion of the cover 106 of FIG. 1. The cover 106 includes the elastomeric film 114 and the attachment device 116. In some embodiments, the elastomeric film 114 may have a plurality of perforations 118 extending through the elastomeric film 114. The plurality of perforations 118 may be apertures having material removed from the elastomeric film 114 or may be slits having an opening but not material removal. In one illustrative embodiment, each perforation 118 of the plurality of perforations 118 creates an opening having an average effective diameter in the range of about 0.05 mm to about 0.40 mm. An effective diameter is a diameter of a circular area having the same surface area as a corresponding non-circular area. In another illustrative embodiment, a portion of the material forming the elastomeric film 114 may be removed to form each perforation 118 of the plurality of perforations 118. The total surface area of the removed portion of material may average between about 0.2% to about 13% of the total surface area of the elastomeric film 114.

The plurality of perforations 118 may cover all of the elastomeric film 114 or a portion of the elastomeric film 114. The plurality of perforations 118 may have a pitch between adjacent perforations 118. The pitch is a measurement of the repeated distance between adjacent perforations 118 having translational symmetry. For example, if a surface of the elastomeric film 114 is described by two orthogonal lines, the pitch describes the distance between adjacent perforations 118 parallel to the two orthogonal lines. The pitch of the plurality of perforations 118 is typically between about two times and about six times a thickness of the attachment device 116. For example, the attachment device 116 may have a thickness of about 0.5 mm and a pitch of the plurality of perforations 118 in the elastomeric film 114 may be between about 1.0 mm and about 3.0 mm. The pitch can vary between the two orthogonal directions, and the pitch can be non-uniform in each direction. In some embodiments, the pitch may have gaps in the pattern of perforations 118 described by the pitch.

The attachment device 116 may be coated onto a side of the elastomeric film 114. The attachment device 116 may generally be continuous and coextensive with the elastomeric film 114. As a result, the plurality of perforations 118 may be covered by the attachment device 116. Covering of the plurality of perforations 118 by the attachment device 116 may prevent leaks through the plurality of perforations 118

The plurality of perforations 118 may expose the attachment device 116 from an un-coated side of the elastomeric film 114. Exposure of the attachment device 116 permits the switching solution to be applied to the attachment device 116 through the elastomeric film 114. In some embodiments, the size and distribution of the plurality of perforations 118 can be used to control the rate of interaction between the switching solution and the attachment device 116.

If no material is removed to form the perforations 118, the perforations 118 may be slits such as half-moon slits. As slits, the plurality of perforations 118 act as small valves, and act to minimize exposure of the attachment device 116 to the un-coated side of the elastomeric film 114. If the drape material is removed to form the plurality of perforations 118, the attachment device 116 may extend through the perforations 118 and causes a tackiness to be experienced on an un-coated side of the elastomeric film 114. In this case, a release liner be applied and left in place to cover the perforations 118 on a side of the elastomeric film 114 until removal of the cover 106 is desired. Alternatively, a powder or sealing agent may be applied on a side of the elastomeric film 114.

In some embodiments, the plurality of perforations 118 may be formed by a user during use of the cover 106. For example, a hand tool may be provided with the cover 106. If a user desires to remove the cover 106 from a tissue site 101, the hand tool can be used to form the a plurality of perforations 118. For example, the hand tool may be a device having a roller with one or more scalpets disposed on the roller. The roller may be rolled across the elastomeric film 114, permitting the scalpets to form the plurality of perforations 118 in the elastomeric film 114. After formation of the plurality of perforations, the switching solution is applied over the perforations 118 to transition the attachment device 116 from the first bond strength to the second bond strength.

Figure 3:
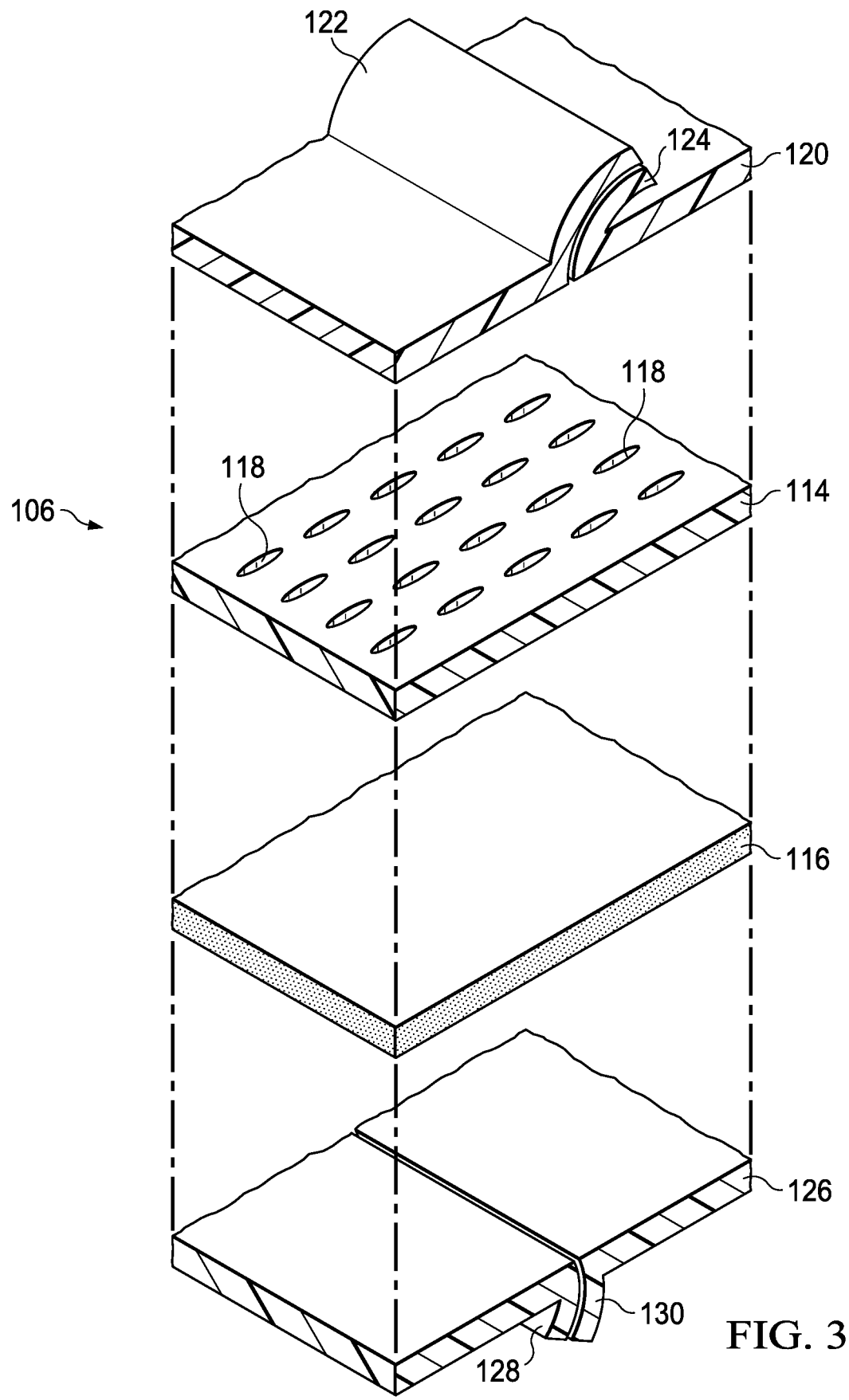
FIG. 3 is an exploded perspective view of a portion of an illustrative embodiment of the cover.

FIG. 3 is an exploded perspective view of a portion of the cover 106, illustrating additional details that may be associated with some embodiments of the therapy system 100. A first side of the elastomeric film 114 may be covered by a first release liner 120. The first release liner 120 may be a material that seals the surface of or provides additional handling rigidity to the elastomeric film 114. The first release liner 120 may also be a material that is removable. The first release liner 120 may comprise one or more of the following: a polyurethane film, high density polyethylene, a high-MVTR film, polymers such as acrylic copolymers, polyvinyl acetate, polyether block amide copolymers (PE-BAX), polyvinyl alcohol and copolymers, polyamide, polyvinylchloride, or polyvinylidene chloride. In some embodiments, the first release liner 120 may be a two-part member having a first gripping portion 122 and a second gripping portion 124 to facilitate removal. The first release liner 120 may be retained only during deployment of the elastomeric film 114 and then removed. Alternatively, the first release liner 120 may remain in place covering the plurality of perforations 118 until removal of the elastomeric film 114 from the tissue site 101 is desired. In this latter situation, the first release liner 120 prevents accidental exposure of the attachment device 116 to a switching solution through the plurality of perforations 118.

A second release liner 126 may be used to cover a side of the attachment device 116 opposite the elastomeric film 114. The second release liner 126 may be similar to and operate as described above with respect to the first release liner 120. The second release liner 126 can be removed before the attachment device 116 is deployed against the epidermis 103 adjacent the tissue site 101. The second release liner 126 may include a first gripping member 128 and a second gripping member 130 to facilitate removal of the second release liner 126 from the attachment device 116.

The cover 106 may be formed in numerous ways. According to one illustrative embodiment, the elastomeric film 114 is formed from a drape material. The plurality of perforations 118 are then formed through the elastomeric film 114 by punching, cutting, or drilling, for example. The attachment device 116 can be applied to a side of the elastomeric film 114. The first release liner 120 can be applied to a side of the elastomeric film 114 that is opposite the attachment device 116. The second release liner 126 can be applied to a side of the attachment device 116 that is opposite the elastomeric film 114.

In operation, the tissue interface 108 is deployed adjacent to the tissue site 101. The cover 106 is deployed over the tissue interface 108 and a portion of the epidermis 103 adjacent to the tissue site 101 to create a sealed therapeutic environment. If not already applied, the dressing interface 110 is applied to provide fluid communication from a point exterior of the cover 106 to the sealed therapeutic environment. The tube 112 is fluidly coupled between the dressing interface 110 and the negative-pressure source 104. The negative-pressure source 104 is activated and fluid is drawn from the sealed therapeutic environment through the tissue interface 108 to generate a negative pressure. After a desired treatment time has passed, the cover 106 can be removed.

The cover 106 can be removed by removing the first release liner 120, if applicable, and applying the switching solution on the cover 106. The switching solution travels through the plurality of perforations 118 in the elastomeric film 114 and wets the attachment device 116. Wetting the attachment device 116 with the switching solution can cause the bond strength of the attachment device 116 to transition from the first bond strength to the second bond strength. The cover 106 is then removed from the tissue site 101 and the epidermis 103.

Figure 4:
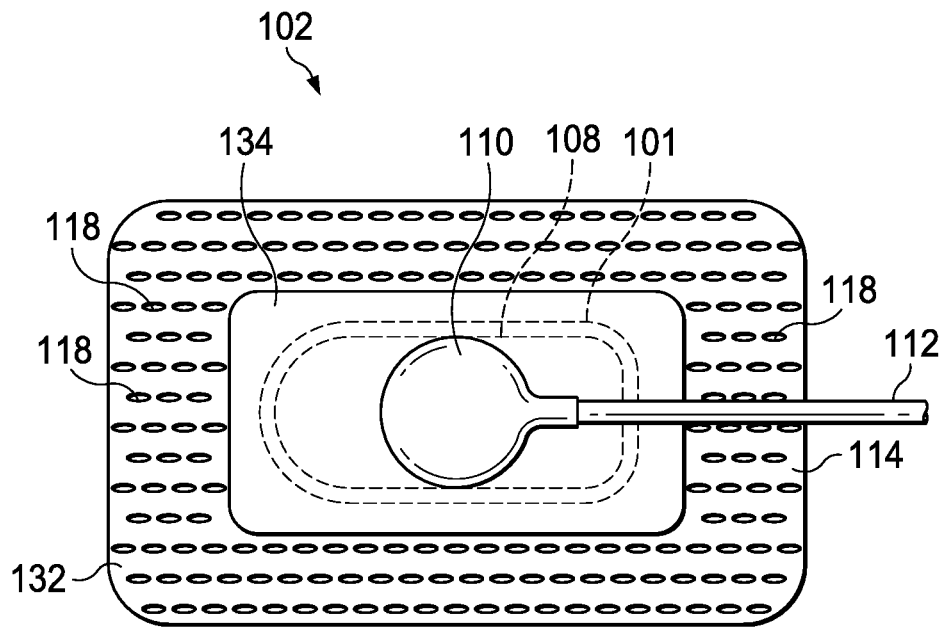
FIG. 4 is a plan view of a portion of an illustrative embodiment of a system for treating a tissue site on a patient that employs an illustrative cover.

FIG. 4 is a plan view of a portion of the dressing 102, illustrating another cover 106 that can be used with the therapy system 100 of FIG. 1. As shown in FIG. 4, the cover 106 is disposed over the tissue site 101 and the tissue interface 108. The dressing interface 110 may be coupled to the cover 106, and the tube 112 may be coupled between the dressing interface 110 and the negative-pressure source 104. The cover 106 of FIG. 4 is similar to and includes the features of the cover 106 of FIG. 1, FIG. 2, and FIG. 3. The cover 106 of FIG. 4 can include a peripheral portion 132 and a central portion 134. The peripheral portion 132 is an outer band on the elastomeric film 114 that is sized to be exclusively or nearly exclusively over the epidermis 103 adjacent the tissue site 101. The central portion 134 of the elastomeric film 114 is over the tissue site 101. The plurality of perforations 118 are formed through the peripheral portion 132 of the elastomeric film 114, and the central portion 134 does not have the perforations 118. The attachment device 116 (not shown) is applied to the elastomeric film 114. In some embodiments, the attachment device 116 may have a first bond strength on the peripheral portion 132 of the elastomeric film 114, and a second bond strength on the central portion 134. The first bond strength of the attachment device 116 on the peripheral portion 132 may be greater than the second bond strength of the attachment device 116 on the central portion 134.

In some illustrative embodiments, the perforations 118 may be located only in certain places or may be located in key places or concentrated in certain places for different effects. For example, as explained in connection with FIG. 4, the perforations 118 may only be in the peripheral portion 132. In addition, the perforations 118 may also be concentrated to form tear lines or tear patterns. The tear patterns or tear lines allow the cover 106 to be torn by hand along the tear line or tear pattern. In this way, the cover 106 may be sized by hand without separate tools. In some embodiments, the perforations 118 may be located, for example, over a joint, to facilitate stretching of the cover 106.

FIG. 5 is a cross-sectional view of a cover 206, illustrating additional details that may be used with some embodiments of the therapy system 100 of FIG. 1. The cover 206 can include an elastomeric film 214, an attachment device 216, and a plurality of perforations 218. The elastomeric film 214, the attachment device 216, and the plurality of perforations 218 may be similar to and operate as described above with respect to the elastomeric film 114, the attachment device 116, and the plurality of perforations 118. The cover 206 can also include polymer particles such as a plurality of expansion members 220. The plurality of expansion members 220 can be disposed in the attachment device 216. In some embodiments, the expansion members 220 can be a compressed foam, such as a polyvinyl acetate foam. The foam can be compressed and cooled below a transition temperature to fix a set of the foam. The set may be a compressed state of the foam that can be released in response to exposures of the compressed foam with a plasticizer. A plasticizer may be a substance or external force, such as the switching solution, that can cause the compressed foam to plasticize and release the set of the foam. In some embodiments, the expansion members 220 can be set to expand preferentially in a particular direction. For example, each expansion member 220 may be compressed in a first direction and uncompressed in a second direction. If the expansion member 220 interacts with the plasticizer, such as the switching solution, the foam that was compressed in the first direction may expand, while the foam that was not compressed in the second direct may remain static. The expansion members 220 can be disposed in the attachment device 216 so that the first direction is oriented in a desired direction of expansion. For example, the expansion members 220 can be configured to expand primarily perpendicularly to a surface of the elastomeric film 214. If activated by the plasticizer, the expansion members 220 can expand in the first direction, perpendicular to a surface of the elastomeric film 214.

The expansion members 220 may also contain a foaming agent, such as a bicarbonate salt. If using a bicarbonate salt, the switching solution may include water and a weak acid (such as citric acid). If the water and the weak acid come into contact with the bicarbonate salt, carbon dioxide gas is released. Release of carbon disoxide gas into the attachment device 216 can provide an expanding force.

In operation, if the cover 206 is to be removed from a tissue site, the switching solution can be applied to the attachment device 216 through the plurality of perforations 218 in the elastomeric film 214. The switching solution may interact with the expansion members 220, causing the expansion members 220 to expand. As the expansion members 220 expand at least partially perpendicularly to the epidermis 103 adjacent the tissue site 101, the elastomeric film 214 may lift away from the attachment device 216. The switching solution may also weaken the attachment device 216. Lifting of the elastomeric film 214 from the attachment device 216 and weakening of the attachment device 216 facilitates removal of the cover 206 from the tissue site 101.

FIG. 6 is a cross-sectional view of a cover 306, illustrating additional details that may be used with some embodiments of the therapy system 100 of FIG. 1. The cover 306 is analogous in most respects to the cover 106 of FIG. 1, FIG. 2, and FIG. 3, and includes an elastomeric film 314, an attachment device 316, and a plurality of perforations 318. The elastomeric film 314, the attachment device 316, and the plurality of perforations 318 may be similar to and operate as described above with respect to the elastomeric film 114, the attachment device 116, and the plurality of perforations 118 of FIG. 1, FIG. 2, and FIG. 3. The cover 306 can include a soluble layer 320. The soluble layer 320 can be disposed between the elastomeric film 314 and the attachment device 316. A first surface of the soluble layer 320 can contact a surface of the elastomeric film 314, and a second surface of the soluble layer 320 that is opposite the first surface can contact a surface of the attachment device 316.

The soluble layer 320 is such that when the switching solution or another solution (for example, water or aqueous solutions) is applied, the soluble layer 320 dissolves, or substantially dissolves, thereby loosening a grip of the soluble layer 320 on the attachment device 316. In this way, the elastomeric film 314 may be quickly removed. The soluble layer 320 may also keep the attachment device 316 from entering the plurality of perforations 318 during manufacture.

Figure 7:
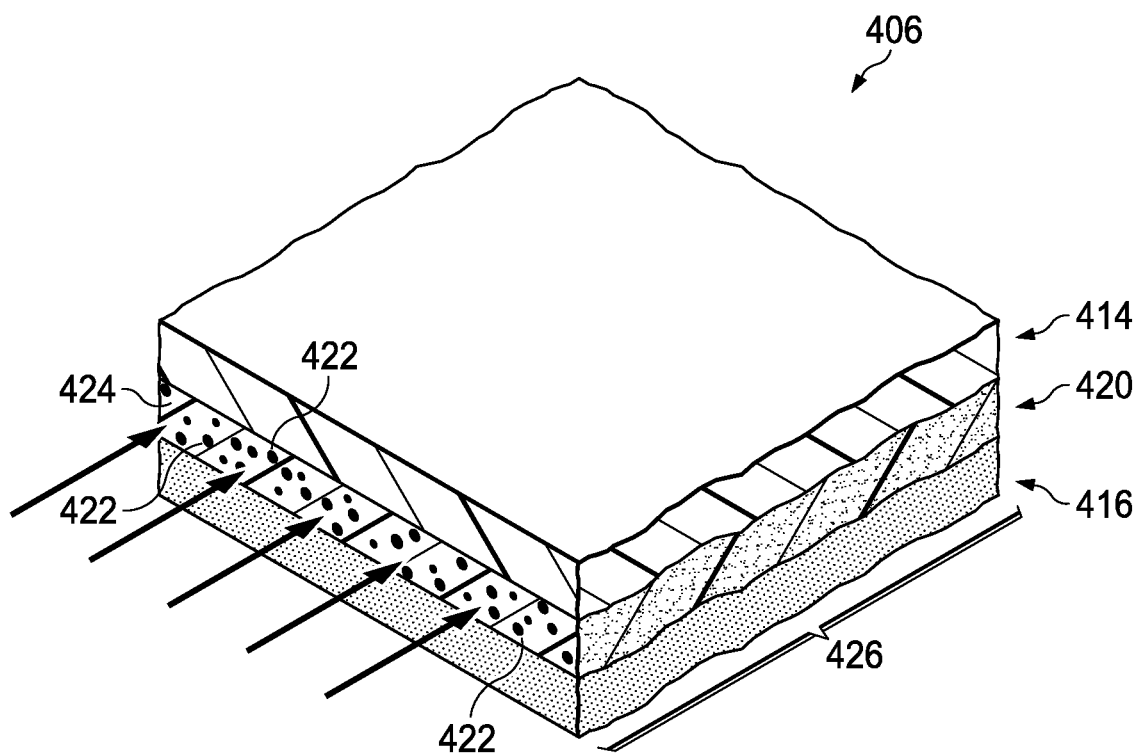
FIG. 7 is a perspective view (with a portion shown in cross section) of another cover that can be used with the system of FIG. 1.

FIG. 7 is a perspective view (with a portion shown in cross section) of a cover 406 that can be used with the therapy system 100 of FIG. 1. The cover 406 is similar to and includes similar components as the cover 106 of FIG. 1. For example, the cover 406 can include an elastomeric film 414 and an attachment device 416. The elastomeric film 414 and the attachment device 416 may be similar to and operate as described above with respect to the elastomeric film 114 and the attachment device 116 of FIG. 1, FIG. 2, and FIG. 3. The elastomeric film 414 preferably does not include a plurality of perforations. The cover 406 can include a wicking layer 420. The wicking layer 420 may be disposed between the elastomeric film 414 and the attachment device 416. The wicking layer 420 may have a first surface in contact with a surface of the elastomeric film 414, and a second surface, which is on an opposite side of the wicking layer 420 from the first surface, in contact with a surface of the attachment device 416. The wicking layer 420 may be a lightweight, open material that is woven or non-woven. In some embodiments, the wicking layer 420 comprises a plurality of threads 422. The plurality of threads 422 of the wicking layer 420 may be continuous, may be scatter coated, or randomly distributed in the wicking layer 420. If the plurality of threads 422 are randomly distributed, the random distribution may disrupt leak paths that may occur from a perimeter to a center of the cover 406.

The wicking layer 420 may have an end 424. The end 424 may be an end of the wicking layer 420 having corresponding ends of the plurality of threads 422 that are exposed. A switching solution may be applied to the end of the wicking layer 420. In response, the plurality of threads 422 may transport the switching solution from the end 424, for example using capillary action, to at least a peripheral portion 426 of the attachment device 416. The peripheral portion 426 of the attachment device 416 may be similar to the peripheral portion 132 of the cover 106. For example, the peripheral portion 426 of the attachment device 416 may be an outer band of the attachment device 416 that is sized to be exclusively or nearly exclusively over the epidermis 103 adjacent the tissue site 101. The wicking layer 420 moves the switching solution from the end 424 inboard, exposing the attachment device 416 to the switching solution. In some embodiments the wicking layer 420 may permit fluid communication across the wicking layer 420. The attachment device 416 may seal the wicking layer 420 from the tissue site 101 so that fluid flowing across the wicking layer 420 may not be in fluid communication with the tissue site 101. Fluid flow through the wicking layer 420 is to the dressing interface 110, preventing a leak path from the tissue site 101 to the external environment. In some embodiments, the wicking layer 420 may be laminated with a solvent soluble coating to control gaseous fluid flow through the wicking layer 420.

In operation, the tissue interface 108 can be disposed over the tissue site 101 and then the cover 406 can be applied over the tissue interface 108 and a portion of the epidermis 103 adjacent to the tissue site 101 to form a sealed space. Negative pressure is applied to the sealed space to provide a negative-pressure treatment. When a desired treatment time has elapsed, a user can apply the switching solution to the end 424 of the wicking layer 420. The plurality of threads 422 can wick the switching solution into the wicking layer 420. The switching solution can flow through the wicking layer 420 and into contact with the attachment device 416. The attachment device 416 can be wetted by the switching solution on at least the peripheral portion 426 of the attachment device 416. As a result, the bond strength of the attachment device 416 can transition from the first bond strength to the second bond strength. After the attachment device transitions to the second bond strength, the elastomeric film 414 can be removed.

Figure 8:
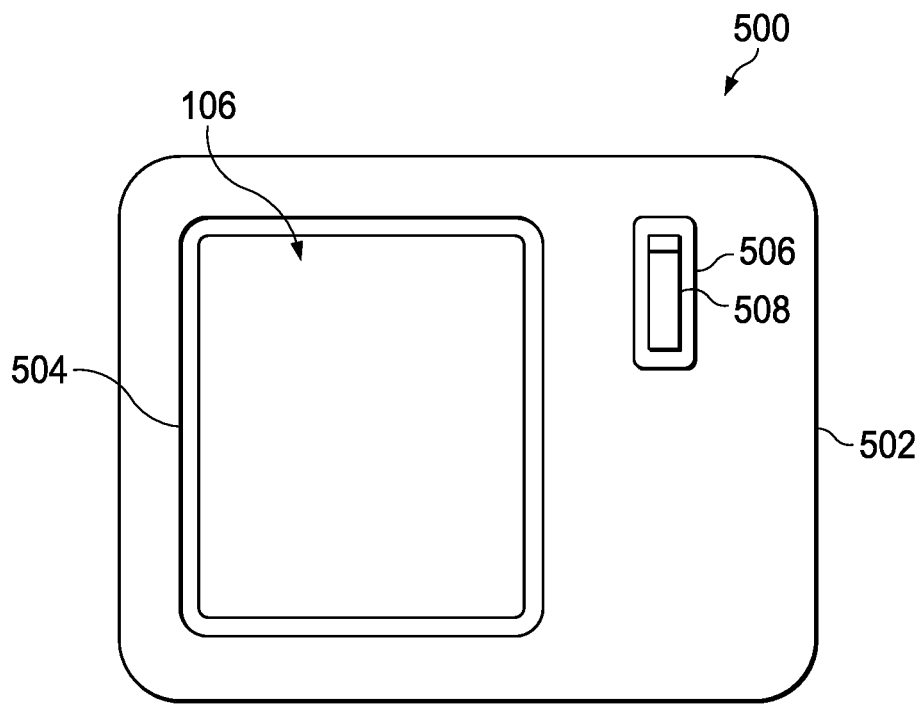
FIG. 8 is a plan view of a kit for forming a seal over the portion of a patient's body.

FIG. 8 is a plan view of a kit 500 including the cover 106 for forming a seal over the tissue site 101. The kit 500 may have a package or container 502. The container 502 may have a first compartment 504 for receiving the cover 106. The container 502 may have a second compartment 506 for receiving a container, vial 508, wipe, bottle, or other item containing the switching solution. Another compartment (not shown) may be added to include skin preparation materials. For example, sealed skin preparation wipes may be disposed in the second compartment 506. One skin preparation wipe may be used to prepare the epidermis 103 surrounding the tissue site 101 and another wipe may be used to rub across the elastomeric film 114 of the cover 106 to remove the cover 106.

Figure 9:
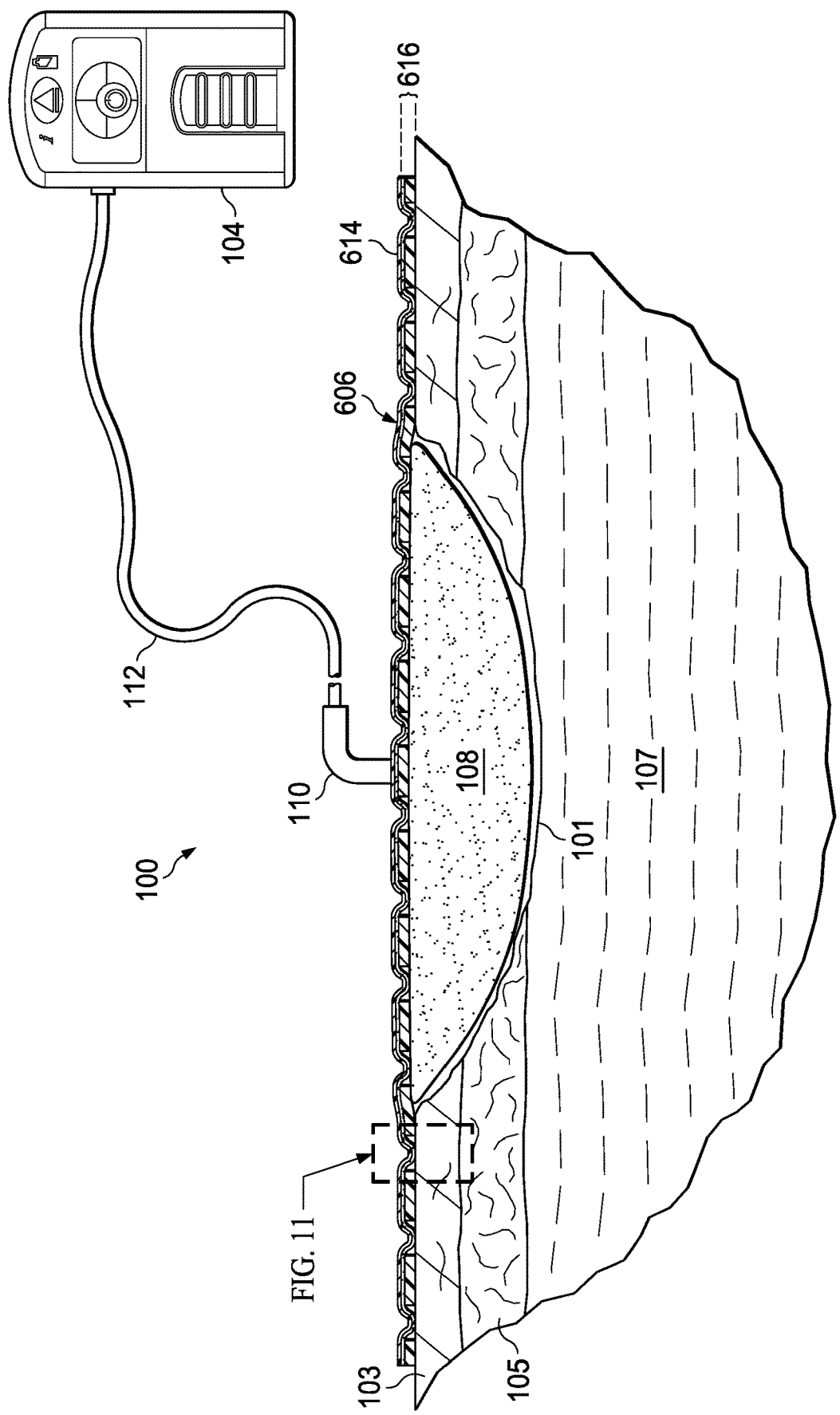
FIG. 9 is a cross-sectional view (with a portion shown in elevation) of another cover for use with the system for treating a tissue site on a patient with negative pressure of FIG. 1.

FIG. 9 is a cross-sectional view (with a portion shown in elevation) of another cover 606 for use with the therapy system 100 for treating a tissue site on a patient with negative pressure of FIG. 1. The therapy system 100 includes the negative-pressure source 104, the tube 112, the dressing interface 110, and the tissue interface 108 disposed over the tissue site 101 through the epidermis 103, the dermis, 105, and into the subcutaneous tissue 107. The cover 606 may be similar to the cover 106 of FIG. 1, FIG. 2, and FIG. 3 and includes an elastomeric film 614 and an attachment device 616. The elastomeric film 614 may be similar to the elastomeric film 114 described above with respect to FIG. 1.

The cover 606 can be disposed over the tissue interface 108 and at least a portion of the tissue site to form a sealed space. The sealed space contains the tissue interface 108. The negative-pressure source 104 is fluidly coupled to the sealed space through the dressing interface 110 to provide negative pressure.

Figure 10:
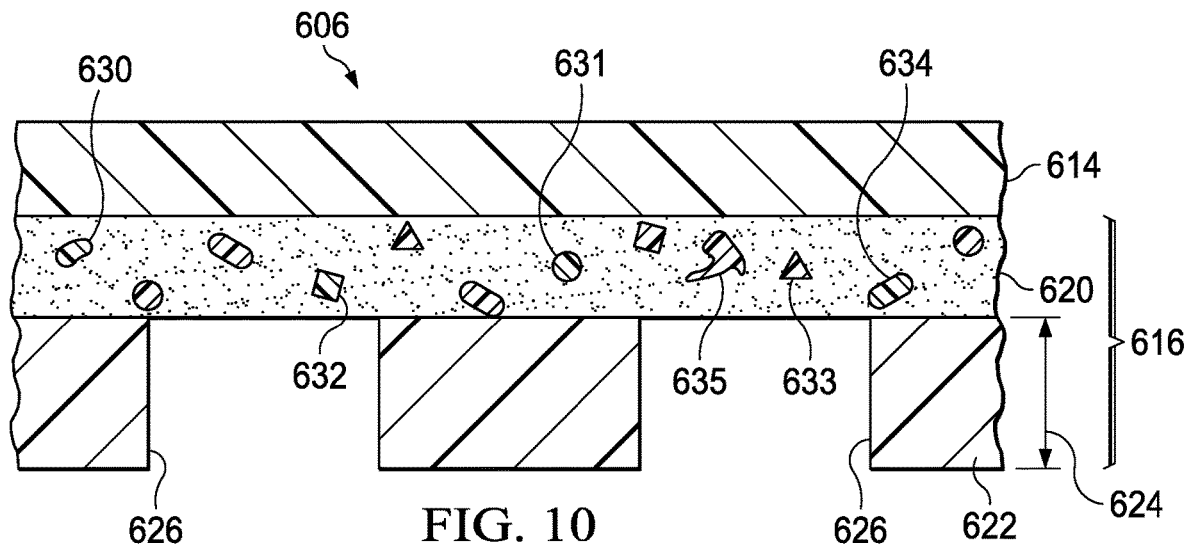
FIG. 10 is a detail in cross section of a portion of the cover of FIG. 9, illustrating additional details that may be associated with some embodiments.

FIG. 10 is a cross section of a portion of the cover 606 of FIG. 9, illustrating additional details that may be associated with some embodiments. The attachment device 616 includes a first adhesive layer 620 and a second adhesive layer 622. Adjacent to the elastomeric film 614 is the first adhesive layer 620. The first adhesive layer 620 has a first side in contact with the elastomeric film 614 and a second side facing away from the elastomeric film 614. The first adhesive layer 620 may be any medically-acceptable, pressure-sensitive adhesive. For example, the first adhesive layer 620 may be an acrylic adhesive layer comprised of an acrylic adhesive, rubber adhesive, high-tack silicone adhesive, polyurethane, or other substance. In an illustrative example, the first adhesive layer 620 comprises an acrylic adhesive with a coating weight of 15 grams/m$^2$ (gsm) to 70 grams/m$^2$ (gsm). In some embodiments, the first adhesive layer 620 may have a first bond strength of about 8 N/cm measured on a stainless steel substrate at 23° C. at 50% relative humidity based on the American Society for Testing and Materials ("ASTM") standard ASTM D3330.

In some embodiments, the first adhesive layer 620 may be a continuous layer of material. In other embodiments, the first adhesive layer 620 may have apertures (not shown). The apertures may be formed after application of the first adhesive layer 620 or may be formed by coating the first adhesive layer 620 in patterns on a carrier layer, e.g., a side of the elastomeric film 614. The apertures in the first adhesive layer 620 may be sized to help control the resultant bond between the epidermis 103 and the first adhesive layer 620. The apertures may also be sized to enhance the MVTR of the cover 606.

The second adhesive layer 622 has a first side in contact with the first adhesive layer 620 and a second side opposite the first side. The second adhesive layer 622 is a soft material that provides a good seal with the epidermis 103. The second adhesive layer 622 may comprise a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (e.g., 30 gsm-70 gsm acrylic), polyurethane, polyolefin, or hydrogenated styrenic copolymers. The second adhesive layer 622 may have a thickness 624 that is typically in the range of about 500 microns (μm) to about 1000 microns (μm). The second adhesive layer 622 may have stiffness between about 5 Shore OO and about 80 Shore OO. The second adhesive layer 622 may be hydrophobic or hydrophilic. In some embodiments, the second adhesive layer 622 may have a bond strength of about 2 N/cm measured on a stainless steel substrate at 23° C. at 50% relative humidity based on the American Society for Testing and Materials ("ASTM") standard ASTM D3330.

The second adhesive layer 622 is formed with a plurality of apertures 626. The apertures 626 may be numerous shapes, for example, circles, squares, stars, ovals, polygons, slits complex curves, rectilinear shapes, triangles, or other shapes. Each aperture 626 of the plurality of apertures 626 has an effective diameter. The average effective diameter of each aperture 626 is typically in the range of about 6 mm to about 50 mm. The plurality of apertures 626 may have a pitch between adjacent apertures 626. The pitch can be the same between adjacent apertures 626, and the pitch can vary in each orthogonal direction. The pitch can be non-uniform in each direction, for example, a spacing between adjacent apertures 626 may be non-repeating or random. In some embodiments, the pitch may have gaps in the pattern of apertures 626 described by the pitch.

In other embodiments, the first adhesive layer 620 may be disposed on the elastomeric film 614 in a first pattern. The second adhesive layer 622 may be deposited directly on the elastomeric film 614 in a second pattern. The second pattern of the second adhesive layer 622 may be registered with the first pattern of the first adhesive layer 620. Registration of the first adhesive layer 620 and the second adhesive layer 622 generally refers to the alignment of the two adhesives relative to one another. In particular, registration of the first adhesive layer 620 and the second adhesive layer 622 may refer to the coordination of adhesive placement on the elastomeric film 614 to achieve a desired effect. For example, a certain percentage of overlap of one adhesive over the other adhesive, minimal overlap of one adhesive over the other adhesive so that the adhesives are offset from one another, or complete overlap of one adhesive over the other adhesive are all adhesive placements that may be considered registered. For example, the first adhesive layer 620 and the second adhesive layer 622 may be registered by being disposed on the elastomeric film 614 so that the first adhesive layer 620 and the second adhesive layer 622 each substantially couple to the elastomeric film 614. In addition, the first adhesive layer 620 and the second adhesive layer 622 may be aligned relative to one another to have minimal overlap of one adhesive over the other adhesive. In another example, the second adhesive layer 622 may be offset from the first adhesive layer 620, with both adhesives being coupled to the elastomeric film 614.

The cover 606 can include a plurality of release agents, such as polymer particles 630. The polymer particles 630 may be formed from polyvinyl acetate, hydroxyl modified acrylics, carboxy modified acrylics, and polyurethanes. The polymer particles 630 may have an average effective diameter of less than about 1 mm. In some embodiments, the polymer particles 630 may have an average effective diameter between about 0.3 mm and about 1 mm. The polymer particles 630 may be formed into a range of shapes. For example, the polymer particles 630 can be spherical 631, tetrahedral or cuboid 632, pyramidal 633, ovular 634, or amorphous 635 in shape.

In some embodiments, the polymer particles 630 may be disposed throughout the first adhesive layer 620. For example, the adhesive forming the first adhesive layer 620 may be provided in a precursor state. In the precursor state, the adhesive of the first adhesive layer 620 may have a viscosity permitting the adhesive of the first adhesive layer 620 to flow similar to a low-viscosity liquid. The polymer particles 630 can be deposited in the adhesive of the first adhesive layer 620 and blended with the adhesive of the first adhesive layer 620. Blending of the polymer particles 630 with the adhesive of the first adhesive layer 620 disposes the polymer particles 630 throughout the first adhesive layer 620 following transition of the adhesive from the precursor state to a cured state to form the first adhesive layer 620.

In other embodiments, the polymer particles may be disposed on a surface of the first adhesive layer 620. For example, the first adhesive layer 620 may have a surface adjacent to the second adhesive layer 622. The polymer particles 630 may be disposed in the surface of the first adhesive layer 620 adjacent to the second adhesive layer 622. A portion of the polymer particles 630 may contact the second adhesive layer 622 or be exposed through the apertures 626. In some embodiments, the polymer particles may make up about 10% or less of a surface area of the surface of the first adhesive layer 620 adjacent to the second adhesive layer 622. The polymer particles 630 can be deposited on the surface of the first adhesive layer 620 by scatter-coating the surface of the first adhesive layer 620 with the polymer particles 630.

In some embodiments, the polymer particles 630 are configured to swell in response to exposure to the switching solution. For example, in response to exposure to the switching solution, each polymer particle 630 may increase in size. The increase in size of each polymer particle 630 can be from about two times to about seven times the original size of the polymer particle 630.

In some embodiments, the polymer particles 630 may dissolve in response to exposure to the switching solution. For example, in response to exposure to the switching solution, the polymer particles 630 may decrease in viscosity. The polymer particles 630 may absorb the switching solution, causing the polymer particles 630 to dissolve. In some embodiments, the polymer particles 630 may be solid prior to exposure to the switching solution and, after exposure to the switching solution, have a viscosity of about $8.9 \times 10^{-4}$ Pa*s. In other embodiments, the polymer particles 630 may have a viscosity between about $8.9 \times 10^{-3}$ Pa*s and about $1.335 \times 10^{-2}$ Pa*s after interaction with the switching solution. As the polymer particles 630 dissolve, the dissolved material of the polymer particles 630 may form a mixture with the switching solution. The mixture may spread along a surface of the first adhesive layer 620. In some embodiments, the mixture may spread over at least 25% of a surface of the first adhesive layer 620. The mixture may decrease the bond strength of the adhesive forming the first adhesive layer 620. For example, after exposure to the mixture, the first adhesive layer 620 may have a second bond strength equal to or less than about ½ N/cm on a stainless steel substrate at 23° C. at 50% relative humidity based on the American Society for Testing and Materials ("ASTM") standard ASTM D3330.

In some embodiments, the polymer particles 630 may both swell and dissolve in response to exposure of the polymer particles 630 to the switching solution. For example, after exposure to the switching solution, the polymer particles 630 may swell, urging the elastomeric film 614 away from the second adhesive layer 622. After swelling, the polymer particles 630 may dissolve, forming the mixture that can spread along a surface of the first adhesive layer 620. In some embodiments, the polymer particles 630 may swell and dissolve in about 5 minutes or less.

In the assembled state, the first adhesive layer 620 is coupled to the elastomeric film 614. The second adhesive layer 622 is coupled to the first adhesive layer 620. There are a number of ways that the cover 606 may be manufactured. The second adhesive layer 622 can be cast onto the first side 160 of a first release liner. The plurality of apertures 626 can be formed through the second adhesive layer 622 and the first release liner. The apertures 626 may be formed using shaped pins that puncture the materials as the materials move along a manufacturing path or by rolling a drum with shaped pins along the materials. The shaped pins are configured to make the desired shape and size of the apertures 626. The first adhesive layer 620 may be cast onto the second adhesive layer 622 opposite of the first release liner. A second release liner may be applied to the first release liner to contact portions of the first adhesive layer 620 that may extend through the apertures 626. The elastomeric film 614 is applied to the first adhesive layer 620.

In another embodiment, the adhesive of the first adhesive layer 620 may be cast onto the elastomeric film 614 to form the first adhesive layer 620. The adhesive of the first adhesive layer 620 can be either dissolved in a solvent or dispersed in a continuous phase, which may be water, and the wet coating is dried to form the first adhesive layer 620 on the elastomeric film 614. The first adhesive layer 620 can be brought into contact with the second adhesive layer 622 with laminating rollers. The cover 606 is then fully assembled and is sterilized and packaged.

Figure 11:
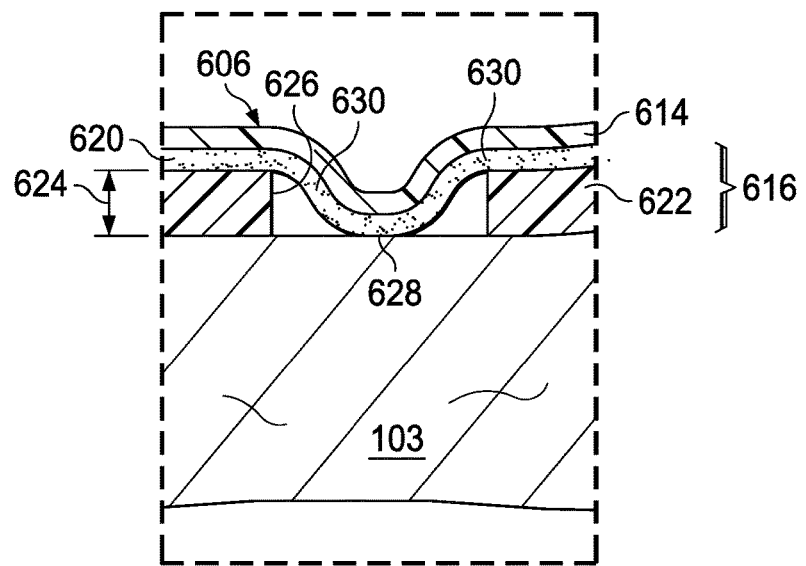
FIG. 11 is a sectional view of a portion of a cover for use with the system of FIG. 9.

FIG. 11 is a sectional view of a portion of the cover 606 for use with the system of FIG. 9. In operation, the cover 606 can be placed over the tissue site 101 and the tissue interface 108 so that a portion of the cover 606 is in contact with the epidermis 103 surrounding the tissue site 101. The second adhesive layer 622 initially couples the cover 606 to the epidermis 103. However, the bond strength of the second adhesive layer 622 is such that the second adhesive layer 622 may hold the cover 606 in place while allowing the cover 606 to be lifted and moved if desired. Once in the desired location, a force can be applied to the elastomeric film 614 of the cover 606. For example, a user may rub the elastomeric film 614 of the cover 606. The force causes at least a portion of the first adhesive layer 620 to be forced into the plurality of apertures 626 and into contact with the epidermis 103, forming contact couplings 628. The bond strength of the first adhesive layer 620 is greater than the bond strength of the second adhesive layer 622 so that the contact couplings 628 provide a bond between the epidermis 103 and the cover 606 that is greater than the bond between the second adhesive layer 622 and the epidermis 103. In some embodiments, the contact couplings 628 may hold the cover 606 in place, permitting the adhesive of the second adhesive layer 622 to flow, filling crevices and gaps to limit flow paths for fluids between the cover 606 and the epidermis 103.

The average effective diameter of the plurality of apertures 626 for the second adhesive layer 622 may be varied as one control of the tackiness or adhesion strength of the cover 606. In this regard, there is interplay between three main variables for each embodiment: the thickness 624, the average effective diameter of the plurality of apertures 626, and the tackiness of the first adhesive layer 620. The more first adhesive layer 620 that extends through the apertures 626, the stronger the bond of the contact coupling 628. The smaller the thickness 624 of the second adhesive layer 622, the more the first adhesive layer 620 generally extends through the apertures 626 and the greater the bond of the contact coupling 628. As an example of the interplay, if an adhesive having a high bond strength is used to form the first adhesive layer 620 and the thickness 624 of the second adhesive layer 622 is small, the average effective diameter of the plurality of apertures 626 may be relatively smaller. In one illustrative, non-limiting embodiment, the thickness 624 may be approximately 200 microns, the first adhesive layer 620 is approximately 30 microns with a bond strength of 2000 gf/25 mm wide strip (approximately 8 N/cm), and the average effective diameter is approximately about 6 mm.

Figure 12A:
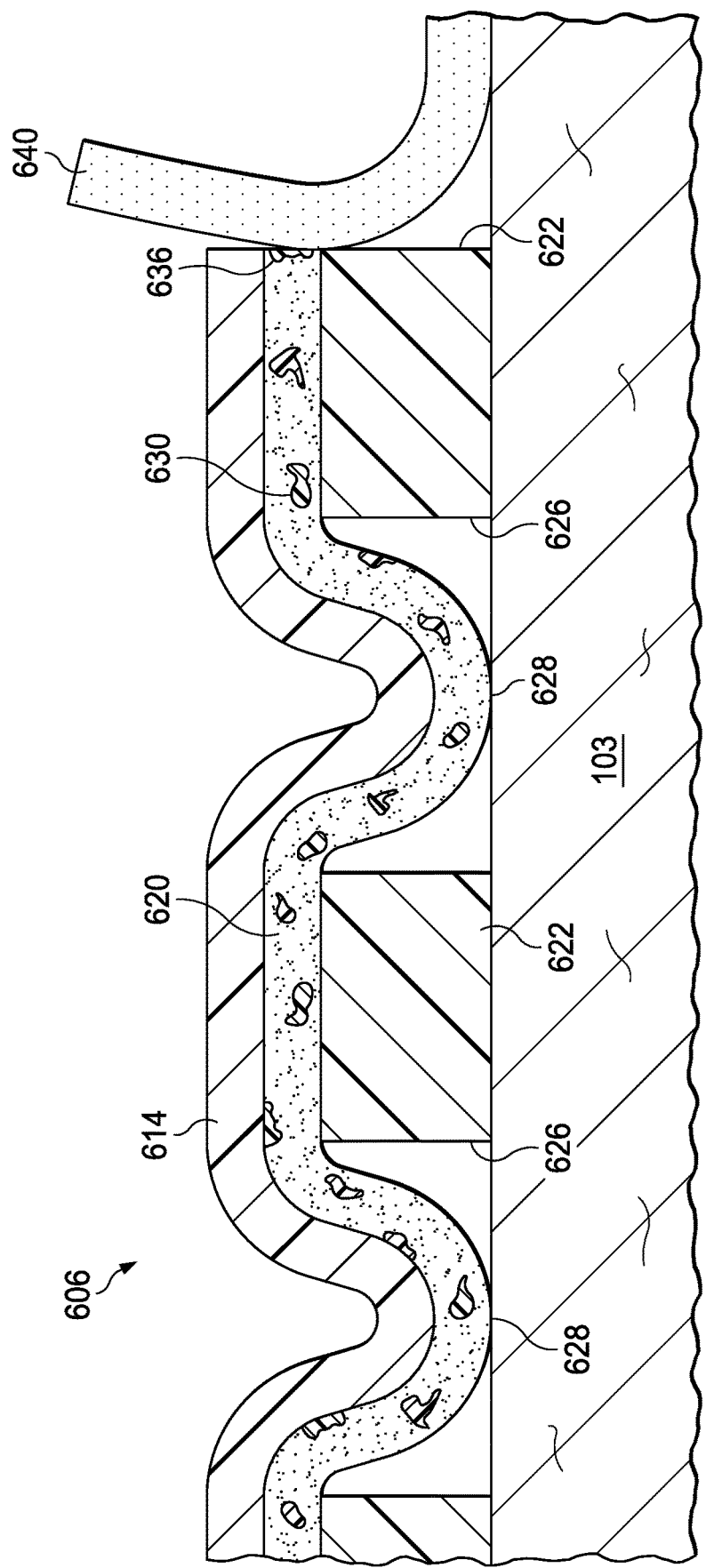
FIGS. 12A, 12B, and 12C are sectional views of a portion of the cover of FIG. 10, during removal of the cover.

FIG. 12A is a sectional view of a portion of the cover 606 of FIG. 10, during removal of the cover 606. If the cover 606 is to be removed, the switching solution may be applied to the cover 606. In some embodiments, the switching solution may be provided in a wipe 640. The wipe 640 may be a woven cloth. The wipe 640 may also be non-woven carrier cloth. The wipe 640 may also be a swab, such as a cotton swab. In other embodiments, the switching solution may be provided in a bottle or vial. The bottle or vial may include a nozzle or other device configured to permit the switching solution contained within the bottle to be applied to an edge of the cover 606. The wipe 640, having the switching solution disposed thereon, may be rubbed along an edge of the cover 606. The polymer particles 630 proximate to the edge of the cover 606 may come in contact with the switching solution as the wipe 640 is applied to the edge of the cover 606. For example, a polymer particle 636, disposed on the edge of the first adhesive layer 620, may be exposed to the switching solution as the wipe 640 is applied along the edge of the cover 606.

Figure 12B:
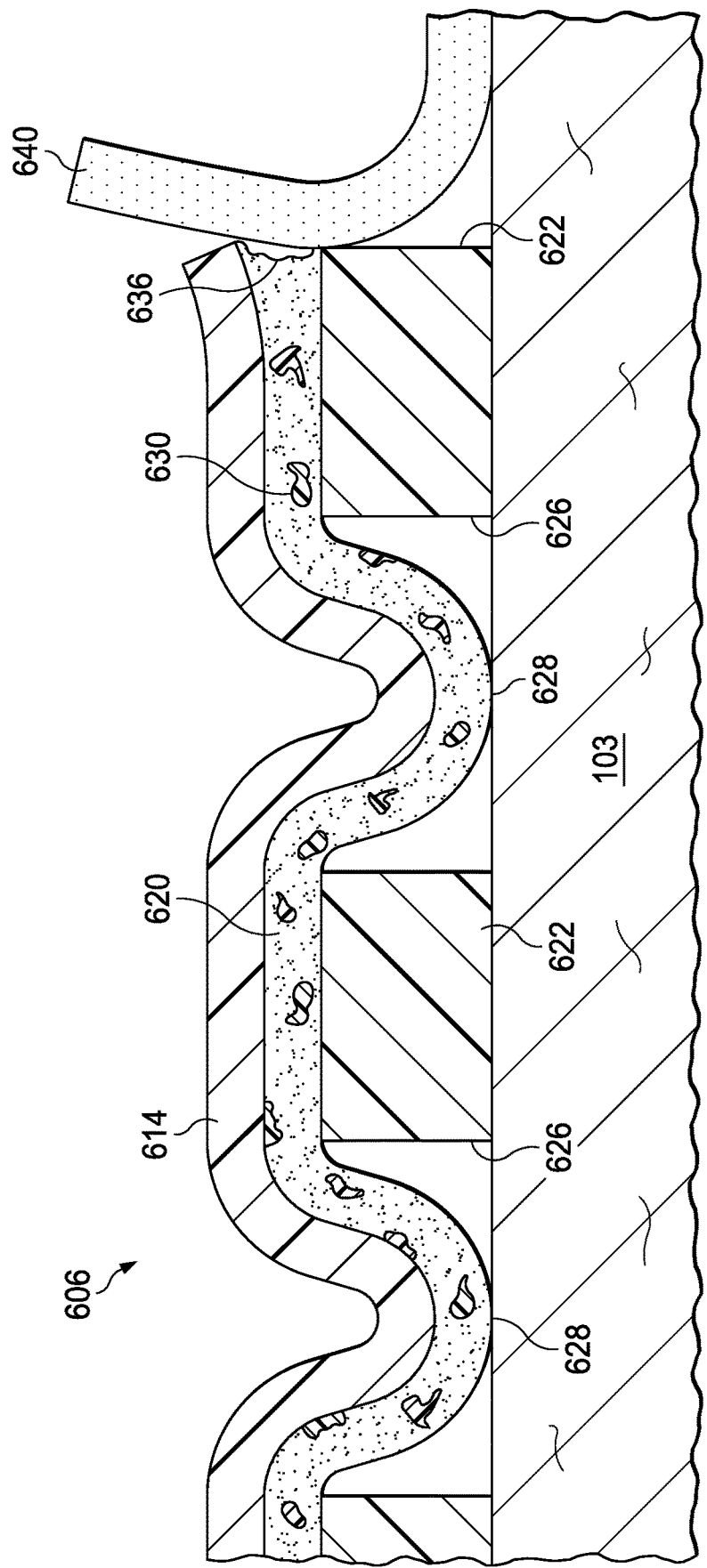

FIG. 12B is a sectional view of the cover 606 of FIG. 12A, illustrating additional details that may be associated with the removal of the cover 606. As the polymer particle 636 is exposed to the switching solution in the wipe 640, the polymer particle 636 may swell. As the polymer particle 636 swells, the elastomeric film 614 may be urged away from the second adhesive layer 622. As the elastomeric film 614 is urged away from the second adhesive layer 622, the elastomeric film 614 may be at least partially separated from the cover 606.

Figure 12C:
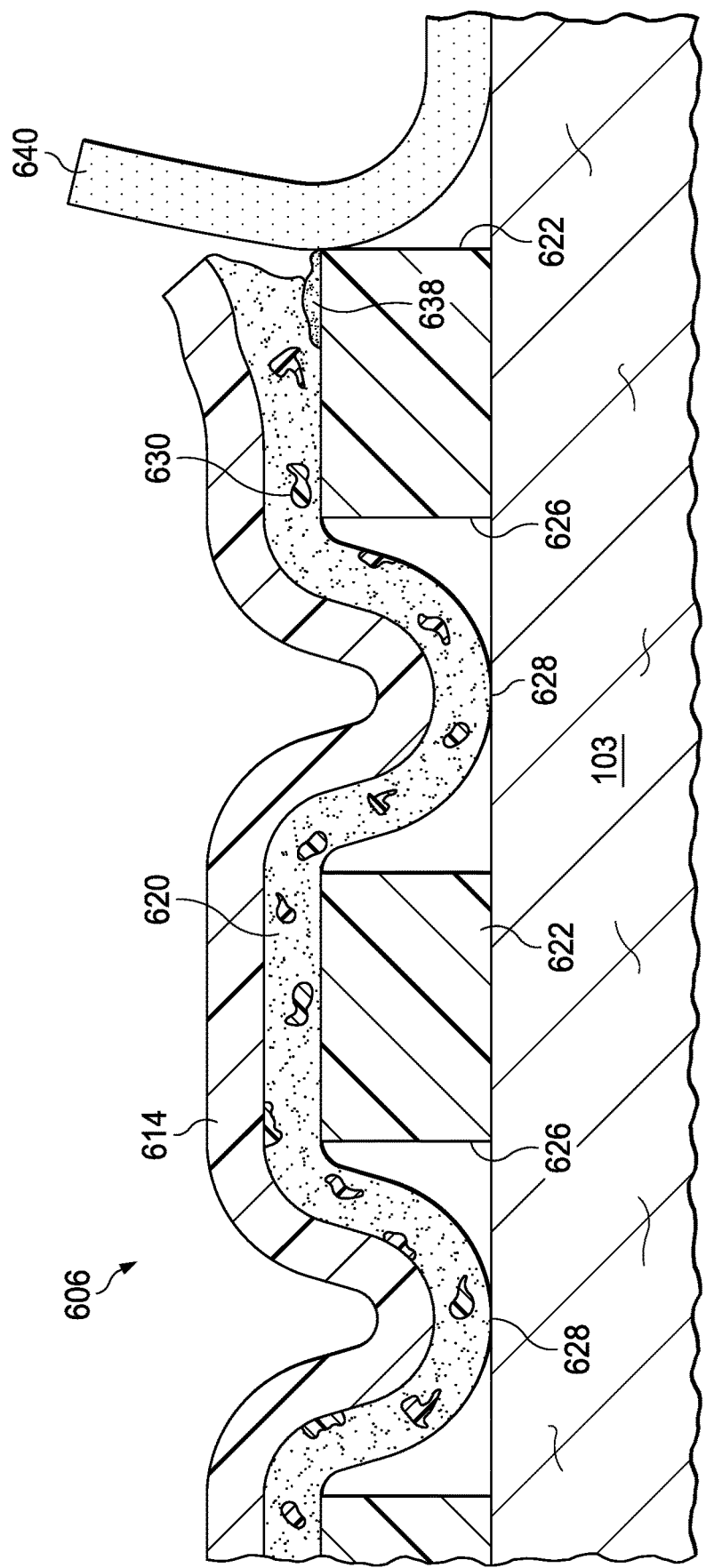

FIG. 12C is a sectional view of the cover 606 of FIG. 12A, illustrating additional details that may be associated with the removal of the cover 606. After the polymer particle 636 swells in response to exposure to the switching solution, the polymer particle 636 can also dissolve. For example, the polymer particle 636 may dissolve after exposure to the switching solution on the wipe 640, forming a mixture 638 comprising the dissolved material of the polymer particle 636 and the switching solution. In some embodiments, the mixture 638 may comprise one or more of: polyvinyl acetate, hydroxyl modified acrylics, carboxy modified acrylics, and polyurethanes mixed with one or more of: alcohols, such as ethanol, methanol, propyl alcohols, such as isopropyl alcohol, isopropanol, and other alcohols such as butanols, esters such as butyl ethanoate (acetate), ketones, such as propanone (acetone), natural oils such as linseed, and soyer. The mixture 638 may flow into areas of the first adhesive layer 620 exposed by the dissolution of the polymer particle 636. In some cases the mixture 638 can flow into areas between the first adhesive layer 620 and the second adhesive layer 622. Exposure of the first adhesive layer 620 to the mixture 638 may transition the adhesive of the first adhesive layer 620 from a first bond strength to a second bond strength. In some embodiments, the second bond strength of the first adhesive layer 620 is less than the first bond strength of the first adhesive layer 620, permitting the first adhesive layer 620 to be separated from the epidermis 103. As the elastomeric film 614 and the first adhesive layer 620 are separated from the epidermis 103, the switching solution may be carried toward a center of the cover 606 by both capillary action and repeated application of the switching solution with the wipe 640 to the cover 606.

Figure 13:
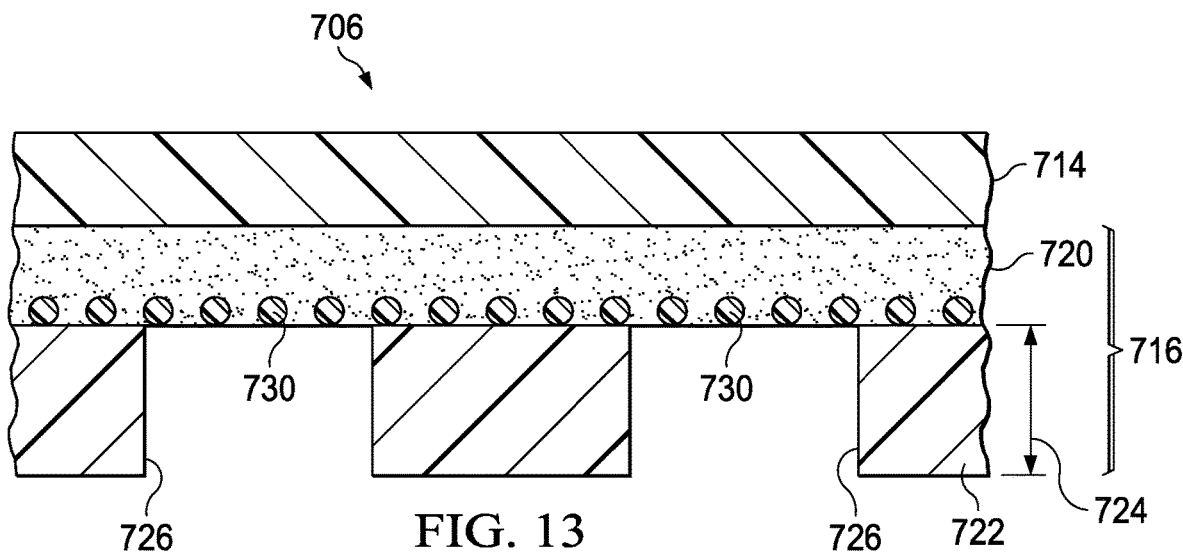
FIG. 13 is a sectional view of a portion of another cover for use with the system of FIG. 9.

FIG. 13 is a sectional view of a portion of a cover 706 for use with the therapy system 100 of FIG. 9. The cover 706 may be similar to the cover 606 of FIG. 10 and may include an elastomeric film 714, and an attachment device 716 having a first adhesive layer 720 and a second adhesive layer 722. The elastomeric film 714, the attachment device 716, the first adhesive layer 720, and the second adhesive layer 722 may be similar to and operate as described above with respect to the elastomeric film 614, the attachment device 616, the first adhesive layer 620, and the second adhesive layer 622. The second adhesive layer 722 may have a thickness 724 and a plurality of apertures 726. The thickness 724 and the plurality of apertures 726 may be similar to and operate as described above with respect to the thickness 624 and the plurality of apertures 626, respectively.

The cover 706 also includes a plurality of fibers 730. The fibers 730 may be formed from polyvinyl acetate, hydroxy modified acrylics, carboxy modified acrylics, and polyurethanes. The fibers 730 may have an average effective diameter of less than about 1 mm. In some embodiments, the fibers 730 may have an average effective diameter between about 0.3 mm and about 1 mm. In still other embodiments, the fibers 730 may have an average effective diameter between about 10 microns and about 30 microns.

The plurality of fibers 730 may be disposed in the first adhesive layer 720. In some embodiments, the plurality of fibers 730 are proximate to a surface of the first adhesive layer 720. As illustrated in FIG. 13, the plurality of fibers 730 may be disposed in the surface of the first adhesive layer 720 that is adjacent to the second adhesive layer 722. The plurality of fibers 730 may comprise between about 2% and about 7% of a surface area of the first adhesive layer 720 that is adjacent to the second adhesive layer 722.

The plurality of fibers 730 may be reactive to the switching solution. For example, the plurality of fibers 730 may swell and dissolve in response to exposure of the plurality of fibers 730 with the switching solution. For example, each fiber 730 of the plurality of fibers 730 may increase in size from about two times to about seven times the original size of the fiber 730. The plurality of fibers 730 may absorb the switching solution, and in response, may decrease in viscosity. In some embodiments, the plurality of fibers 730 may have a viscosity of about $8.9 \times 10^{-4}$ Pa*s, after interaction with the switching solution. In other embodiments, the plurality of fibers 730 may have a viscosity between about $8.9 \times 10^{-3}$ Pa*s and about $1.335 \times 10^{-2}$ Pa*s after interaction with the switching solution. In some embodiments, the liquid formed by dissolving of the plurality of fibers 730 may spread over at least 25% of a surface of the first adhesive layer 720. The plurality of fibers 730 may swell and dissolve in about 5 minutes or less.

In operation, the fibers 730 may be configured wick the switching solution into the first adhesive layer 720 of the cover 706. For example, if the cover 706 is to be removed from a tissue site, the switching solution may be applied to an edge of the cover 706. The plurality of fibers 730 may use capillary action, drawing the switching solution from the edge of the cover 706 into an interior of the cover 706. As the plurality of fibers 730 absorb the switching solution, the plurality of fibers 730 may swell, encouraging separation of the elastomeric film 714 from the second adhesive layer 722. The plurality of fibers 730 may also dissolve. As the plurality of fibers 730 dissolve, the resulting mixture may spread along a surface of the first adhesive layer 720 and in particular along a surface of the first adhesive layer 720 adjacent to the second adhesive layer 722. The mixture formed by the dissolution of the plurality of fibers 730 may decrease the bond strength of the first adhesive layer 720. The decreased bond strength of the first adhesive layer 720 may permit the first adhesive layer 720 and the elastomeric film 714 to be removed from over the tissue site.

Figure 14:
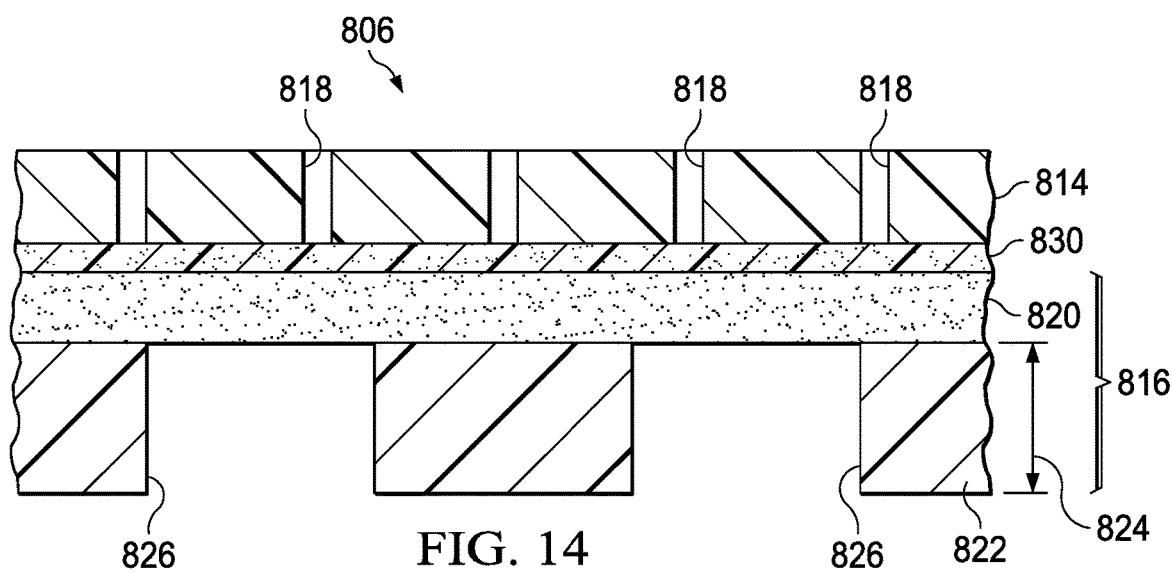
FIG. 14 is a sectional view of a portion of another cover for use with the system of FIG. 9.

FIG. 14 is a sectional view of a portion of a cover 806 for use with the therapy system 100 of FIG. 9. The cover 806 may be similar to the cover 606 of FIG. 10 and may include an elastomeric film 814, and an attachment device 816 having a first adhesive layer 820 and a second adhesive layer 822. The elastomeric film 814, the attachment device 816, the first adhesive layer 820, and the second adhesive layer 822 may be similar to and operate as described above with respect to the elastomeric film 614, the attachment device 616, the first adhesive layer 620, and the second adhesive layer 622. The second adhesive layer 822 may have a thickness 824 and a plurality of apertures 826. The thickness 824 and the plurality of apertures 826 may be similar to and operate as described above with respect to the thickness 624 and the plurality of apertures 626, respectively.

The cover 806 may also include a plurality of perforations 818 extending through the elastomeric film 814 and a polymer layer 830. The plurality of perforations 818 may be similar to and operate as described above with respect to the plurality of perforations 118. The plurality of perforations 818 may each have an average effective diameter between about 0.2 mm and about 0.5 mm. The plurality of perforations 818 can be disposed in a regularly repeating pattern or non-uniformly distributed. In some embodiments, the pitch between adjacent perforations may be about 2 cm.

The polymer layer 830 may be disposed between the elastomeric film 814 and the first adhesive layer 820. The polymer layer 830 may be formed from polyvinyl acetate, hydroxy modified acrylics, carboxy modified acrylics, and polyurethanes. The polymer layer 830 may have thickness of less than about 1 mm. In some embodiments, the polymer layer 830 may have a thickness between about 0.3 mm and about 1 mm. In still other embodiments, the polymer layer 830 may have a thickness between about 10 microns and about 30 microns. The polymer layer 830 may be coextensive with the elastomeric film 814.

The polymer layer 830 may be reactive to the switching solution. For example, the polymer layer 830 may swell and dissolve in response of exposure of the polymer layer 830 to the switching solution. For example, the polymer layer 830 may increase in size from about two times to about seven times the original size of the polymer layer 830. The polymer layer 830 may absorb the switching solution, and in response, may decrease in viscosity. In some embodiments, the polymer layer 830 may have a viscosity of about $8.9 \times 10^{-4}$ Pa*s, after interaction with the switching solution. In other embodiments, the polymer layer 830 may have a viscosity between about $8.9 \times 10^{-3}$ Pa*s and about $1.335 \times 10^{-2}$ Pa*s after interaction with the switching solution. As the polymer layer 830 dissolves, the resulting mixture may spread along a surface of the first adhesive layer 820. In some embodiments, the mixture formed by the dissolution of the polymer layer 830 may spread over at least 25% of a surface of the first adhesive layer 820. The polymer layer 830 may swell and dissolve in about 5 minutes or less.

The polymer layer 830 may prevent fluid communication across the cover 806 through the plurality of perforations 818. By preventing fluid communication through the plurality of perforations 818, the polymer layer 830 can prevent a leak through the plurality of perforations 818 during use of the cover 806. In some embodiments, each perforation 818 may be disposed in the elastomeric film 814 so that each perforation is coincident with the second adhesive layer 822. For example, at each perforation 818, the cover 806 may comprise the second adhesive layer 822, the first adhesive layer 820, the polymer layer 830, and the elastomeric film 814 having a perforation 818. As a result, the perforations 818 may not be aligned or coincident with the plurality of apertures 826. If each perforation is disposed in locations of the elastomeric film 814 over the second adhesive layer 822, the first adhesive layer 820 may have a thickness that is less than a thickness of the first adhesive layer 820 where each perforation 818 is not disposed over the second adhesive layer 822.

To remove the cover 806, the switching solution may be applied to the elastomeric film 814. The switching solution can flow through the perforations 818 to contact the polymer layer 830. The polymer layer 830 can then swell and dissolve, causing the elastomeric film 814 to separate from the first adhesive layer 820. The dissolution of the polymer layer 830 can also weaken the bond strength of the first adhesive layer 820, easing removal of the first adhesive layer 820.

Figure 15:
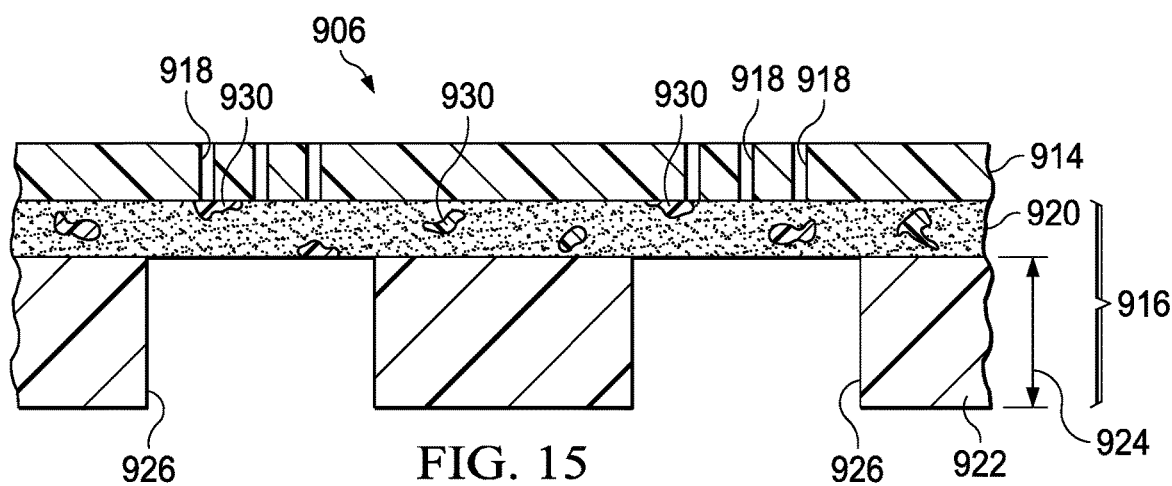
FIG. 15 is a sectional view of a portion of another cover for use with the system of FIG. 9.

FIG. 15 is a sectional view of a portion of a cover 906 for use with the therapy system 100 of FIG. 9. The cover 906 may be similar to the cover 606 of FIG. 10 and may include an elastomeric film 914 and an attachment device 916 having a first adhesive layer 920 and a second adhesive layer 922. The elastomeric film 914, the attachment device 916, the first adhesive layer 920, and the second adhesive layer 922 may be similar to and operate as described above with respect to the elastomeric film 614, the attachment device 616, the first adhesive layer 620, and the second adhesive layer 622. The second adhesive layer 922 may have a thickness 924 and a plurality of apertures 926. The thickness 924 and the plurality of apertures 926 may be similar to and operate as described above with respect to the thickness 624 and the plurality of apertures 626, respectively.

The cover 906 may also include a plurality of perforations 918 extending through the elastomeric film 914 and a plurality of polymer particles 930. The polymer particles 930 may be similar to and operate as described above with respect to the polymer particles 630. In some embodiments, the polymer particles 930 may be disposed throughout the first adhesive layer 920. Some polymer particles 930 may extend across a thickness of the first adhesive layer 920. For example, a polymer particle 930 may have a first end proximate a surface of the first adhesive layer 920 that is adjacent to the elastomeric film 914 and a second end proximate to a surface of the first adhesive layer 920 that is adjacent to the second adhesive layer 922.

In other embodiments, the polymer particles may be disposed on a surface of the first adhesive layer 920. For example, the first adhesive layer 920 may have a surface adjacent to the second adhesive layer 922. The polymer particles 930 may be disposed in the surface of the first adhesive layer 920 adjacent to the second adhesive layer 922. A portion of the polymer particles 930 may contact the second adhesive layer 922 or be exposed through the apertures 926. In some embodiments, the polymer particles may make up about 10% or less of a surface area of the surface of the first adhesive layer 920 adjacent to the second adhesive layer 922. In another example, the first adhesive layer 920 may have a surface adjacent to the elastomeric film 914. The polymer particles 930 may be disposed in the surface of the first adhesive layer 920 adjacent to the elastomeric film 914. A portion of the polymer particles 930 may contact the elastomeric film 914 or be exposed through the perforations 918. In some embodiments, the polymer particles 930 may make up about 10% or less of a surface area of the surface of the first adhesive layer 920 adjacent to the elastomeric film 914. The polymer particles 930 can be deposited on the surface of the first adhesive layer 920 by scatter-coating the surface of the first adhesive layer 920 with the polymer particles 930.

The plurality of perforations 918 may be similar to and operate as described above with respect to the plurality of perforations 118 and the plurality of perforations 818. The plurality of perforations 918 may each have an average effective diameter between about 0.2 mm and about 0.5 mm. In some embodiments, the plurality of perforations 918 may be registered with the plurality of apertures 926. Registration of the plurality of perforations 918 and the plurality of apertures 926 generally refers to the alignment of the perforations and the apertures relative to one another. For example, each perforation 918 may be disposed in the elastomeric film 914 so that the perforation 918 overlies apertures 926.

In some embodiments, each perforation 918 may be disposed in the elastomeric film 914 so that each perforation 918 is coincident with a respective aperture 926. For example, at each perforation 918, the cover 906 may comprise an aperture 926, the first adhesive layer 920 having the polymer particles 930, and the elastomeric film 914 having one or more perforations 918. As a result, the perforations 918 may not be registered with the second adhesive layer 922. In some embodiments, each perforation 918 may be registered with a separate aperture 926. In other embodiments, one or more perforations 918 may be registered with a separate aperture 926. For example, as shown in FIG. 15, three perforations 918 may be registered with a same aperture 926. In other embodiments, groups of perforations 918 greater than or less than three may be registered with each aperture 926.

Figure 16:
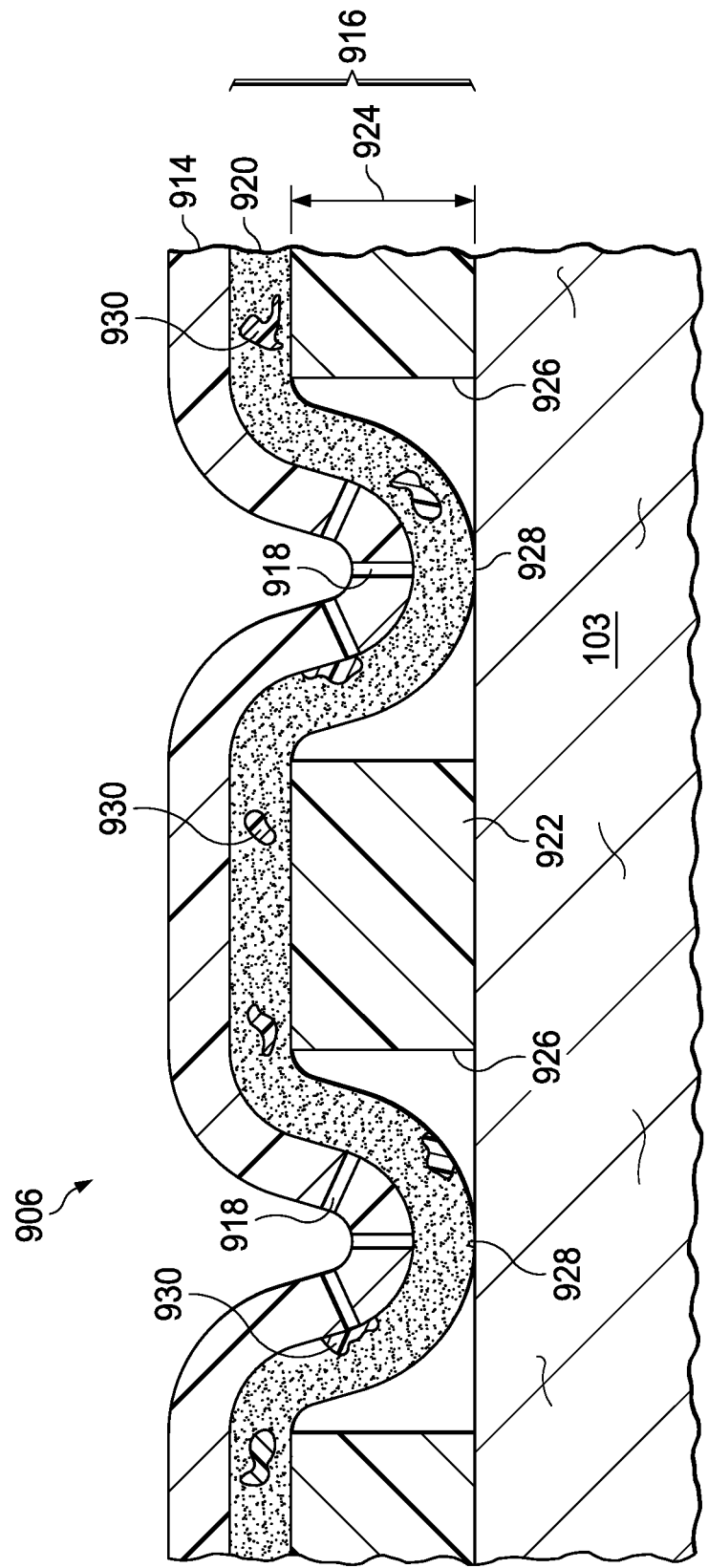
FIG. 16 is a sectional view of a portion of the cover of FIG. 15 during use of the cover.

FIG. 16 is a sectional view of a portion of the cover 906 of FIG. 15, illustrating additional details that may be associated with some embodiments. In operation, the cover 906 can be placed over the tissue site 101 and the tissue interface 108 so that a portion of the cover 906 is in contact with the epidermis 103 surrounding the tissue site 101. The second adhesive layer 922 initially couples the cover 906 to the epidermis 103. The bond strength of the second adhesive layer 922 is such that the second adhesive layer 922 may hold the cover 906 in place while allowing the cover 906 to be lifted and moved if desired. Once in the desired location, a force can be applied to the elastomeric film 914 of the cover 906. For example, a user may rub the elastomeric film 914 of the cover 906. The force causes at least a portion of the first adhesive layer 920 to be forced into the plurality of apertures 926 and into contact with the epidermis 103, forming contact couplings 928. The bond strength of the first adhesive layer 920 is greater than the bond strength of the second adhesive layer 922 so that the contact couplings 928 provide a bond between the epidermis 103 and the cover 906 that is greater than the bond between the second adhesive layer 922 and the epidermis 103. In some embodiments, the contact couplings 928 may hold the cover 906 in place, permitting the adhesive of the second adhesive layer 922 to flow, filling crevices and gaps to limit flow paths for fluids between the cover 906 and the epidermis 103.

Figure 17:
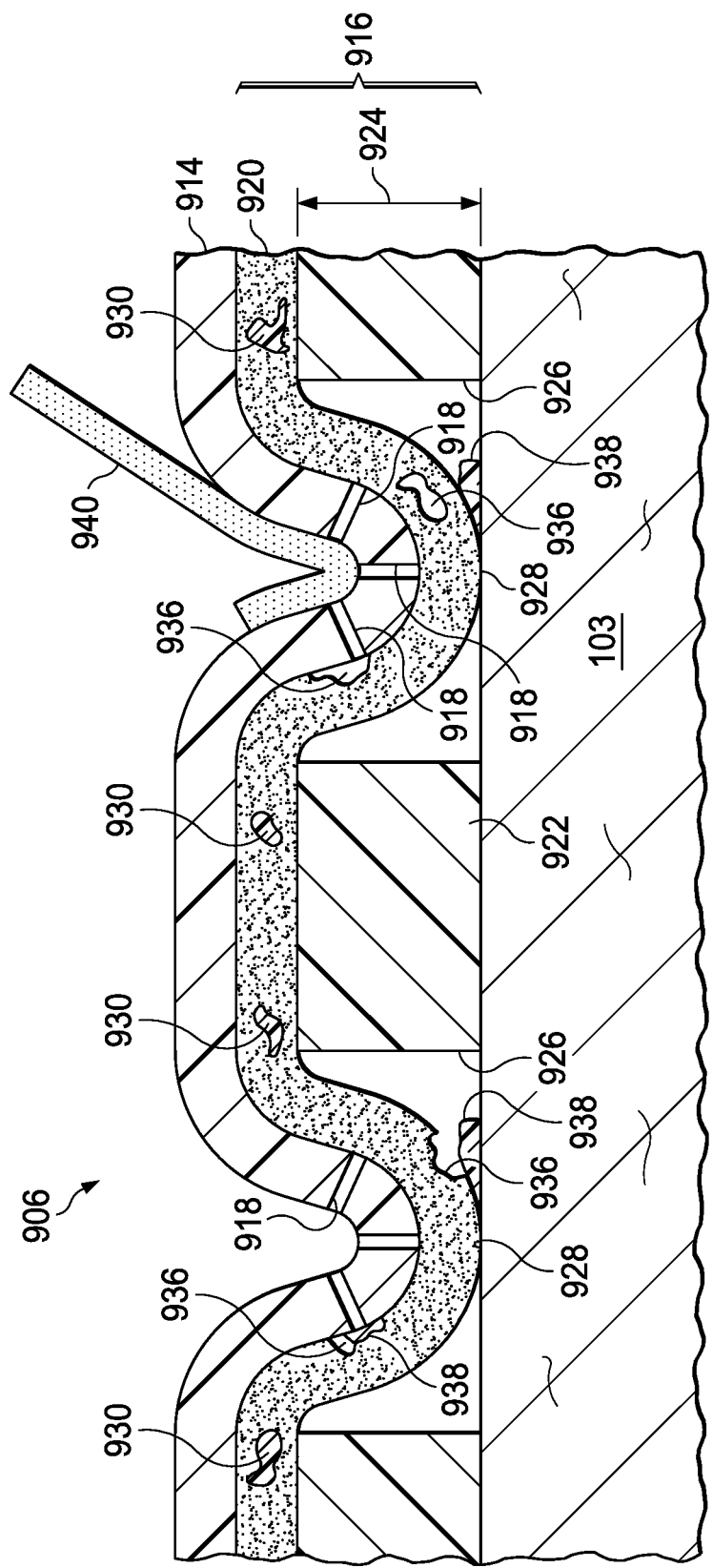
FIG. 17 is a sectional view of a portion of the cover of FIG. 15 during removal of the cover.

FIG. 17 is a sectional view of a portion of the cover 906 of FIG. 15, during removal of the cover 906, illustrating additional details that may be associated with some embodiments. If the cover 906 is to be removed, the switching solution may be applied to the cover 906. In some embodiments, the switching solution may be provided in a wipe 940. The wipe 940 may be similar to and operate as described above with respect to the wipe 640. The wipe 940 may also be a swab, such as a cotton swab. In other embodiments, the switching solution may be provided in a bottle or vial. The bottle or vial may include a nozzle or other device configured to permit the switching solution contained within the bottle to be applied to a surface of the cover 906. The wipe 940, having the switching solution disposed thereon, may be rubbed along the surface of the cover 906. In some embodiments, the wipe 940 may be rubbed or wiped over the perforations 918, depositing the switching solution proximate to the plurality of perforations 918. The switching solution may flow into the plurality of perforations 918; capillary action may also draw the switching solution into and through the plurality of perforations 918.

The polymer particles 930 proximate to the perforations 918 of the elastomeric film 914 may come in contact with the switching solution as the wipe 940 is applied to the surface of the cover 906. As the polymer particles 930 are exposed to the switching solution in the wipe 940, the polymer particles 930 can dissolve. For example, a polymer particle 936 may dissolve after exposure to the switching solution on the wipe 940, forming a mixture 938 comprising the dissolved material of the polymer particle 936 and the switching solution. In some embodiments, the mixture 938 may comprise one or more of: polyvinyl acetate, hydroxyl modified acrylics, carboxy modified acrylics, and polyurethanes mixed with one or more of: alcohols, such as ethanol, methanol, propyl alcohols, such as isopropyl alcohol, isopropanol, and other alcohols such as butanols, esters such as butyl ethanoate (acetate), ketones, such as propanone (acetone), natural oils such as linseed, and soyer. The mixture 938 may flow into areas of the first adhesive layer 920 exposed by the dissolution of the polymer particle 936. In some cases the mixture 938 can flow into areas between the first adhesive layer 920 and the epidermis 103. Exposure of the first adhesive layer 920 to the mixture 938 may transition the adhesive of the first adhesive layer 920 from a first bond strength to a second bond strength. In some embodiments, the second bond strength of the first adhesive layer 920 is less than the first bond strength of the first adhesive layer 920, permitting the first adhesive layer 920 to be separated from the epidermis 103.

In some embodiments, the polymer particles 930 can swell and dissolve, causing the elastomeric film 914 to at least partially separate from the first adhesive layer 920. The dissolution of the polymer particles 930 can also weaken the bond strength of the first adhesive layer 920, easing removal of the first adhesive layer 920. In some embodiments, the switching solution may weaken the bond strength of the first adhesive layer 920 in areas proximate to the perforations 918 and the apertures 926, with which the perforations 918 are registered. Areas of the first adhesive layer 920 that do not have the perforations 918 may maintain the first bond strength. The areas of the second bond strength of the first adhesive layer 920 may overlie the apertures 926 and the contact couplings 928, and areas of the first adhesive layer 920 maintaining the first bond strength may overlie areas of the second adhesive layer 922. Weakening of the contact couplings 928 may permit the cover 906 to be removed without causing trauma or pain to the patient. Maintaining the first bond strength of the first adhesive layer 920 over areas of the second adhesive layer 922 may permit the first adhesive layer 920 to carry the second adhesive layer 922 away from the epidermis as the cover 906 is removed. Registering the perforations 918 with the apertures 926 can permit the polymer particles 930 to provide localized release of the first adhesive layer 920 at locations of the contact couplings 928. Areas of the first adhesive layer 920 coupled to the second adhesive layer 922 may remain coupled to the first adhesive layer 920, and the second adhesive layer 922 may remain coupled to the epidermis 103. As the cover 906 is removed, the bond between the first adhesive layer 920 and the second adhesive layer 922 may be greater than the bond between the second adhesive layer 922 and the epidermis 103, permitting the first adhesive layer 920 to pull the second adhesive layer 922 from the epidermis as the cover 906 is removed.

In some embodiments, dye particles may be disposed in the first adhesive layer 920. For example, dye particles that are barely visible to the naked eye may be disposed in the first adhesive layer 920. For example, the dye particles may have an average effective diameter less than about 0.5 mm and preferably about 0.1 mm. The dye particles may be formed from an ethanol soluble dye. For example, the dye particles may be formed from methylene blue, chlorophylls, anthocyanins, and betalains. Suitable colors may include blues, greens, reds, and yellows. If the switching solution is applied to the dye particles, the dye particles may dissolve and form a visible colored solution. The colored solution may indicate that the switching solution has reached the polymer particles 930, permitting removal of the cover 906. In some embodiments, the dye particles provide a visual indication that the cover 906 may be safely removed without causing trauma to underlying tissue.

The covers described herein can provide numerous advantages over other covers in the art. For example, the polymer particles permit a cover to be constructed using an adhesive having a bond strength substantially greater than a bond strength of adhesives typically used in medical applications. The polymer particles can allow a user to decrease the bond strength of the adhesive so that the cover can be removed from tissue without the pain and trauma normally associated with high bond strength adhesives. By using such an adhesive the potential for the cover to leak also substantially decreases. The covers described herein also provide better sealing capability for difficult tissue sites, such as joints, tissue sites having sensitive or friable tissue surrounding the tissue site, or highly exudating tissue sites. The covers described herein can also be transitioned between bond strengths without the addition of an external energy, such as heat or electromagnetic radiation. As a result, no expensive, reusable and easily lost tools are needed. The covers described herein also do not require the use of any specialty equipment to place or remove the cover. For example, many practitioners are familiar with the use of a wipe to treat a tissue site prior to placement of a cover. Consequently, practitioners do not need to learn how to use specialty equipment. Furthermore, due to the strength of the adhesives used in the covers described herein, a pre-treatment wipe is not needed to clean a tissue site prior to placement of a cover.

Some covers described herein can provide a two-step removal process, permitting a clinician to remove the film layer and the first adhesive layer while leaving the second adhesive layer proximate to the tissue site. The second adhesive layer remaining at the tissue site can be used to provide additional sealing for a subsequent cover placed over the tissue site, or the second adhesive layer can be separately removed. Two-step removal may be trauma and pain free. Other covers described herein provide a one-step removal process, permitting a clinician to remove the film layer, the first adhesive layer, and the second adhesive layer at one time. One-step removal may also be trauma and pain free. One-step removal permits removal of the cover and leaves the tissue substantially free from adhesive residue. One-step removal may also permit the switching solution to be used more effectively by targeting the contact couplings in contact with the tissue and reducing the amount of switching solution that may be required to remove the cover.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing, a container, or both may be eliminated or separated from other components for manufacture or sale. In other example configurations, a controller may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:
1. A sealing member, comprising:
   a film layer having a plurality of perforations extending through the film layer;
   a first adhesive layer coupled to the film layer and covering the plurality of perforations, a tackiness of the first adhesive layer configured to decrease in response to application of a solution to the first adhesive layer;
   a second adhesive layer coupled to the first adhesive layer; and a plurality of apertures extending through the second adhesive layer, each aperture exposing at least a portion of the first adhesive layer through the second adhesive layer.

2. The sealing member of claim 1, wherein the perforations comprise slits having no material removed from the film layer.

3. The sealing member of claim 1, wherein the plurality of perforations have an average effective diameter between about 0.05 mm and about 0.4 mm.

4. The sealing member of claim 1, wherein a surface area of the plurality of perforations is between about 0.2% and about 13% of a surface area of the film layer.

5. The sealing member of claim 1, wherein the perforations comprise half-moon slits.

6. The sealing member of claim 1, wherein the perforations have a pitch in a range of about 1.0 mm to about 3.0 mm.

7. The sealing member of claim 1, wherein the film layer has a thickness in a range of about 5 microns to about 60 microns.

8. The sealing member of claim 1, further comprising a soluble layer coupled to the film layer and the first adhesive layer, the solution being operable to substantially dissolve the soluble layer.

9. A kit for forming a seal over a portion of a patient's body, the kit comprising:
   a drape comprising:
      an outer layer having a first side, a second side, and a plurality of perforations extending through the outer layer,
      a first adhesive covering the plurality of perforations on the second side of the outer layer,
      a second adhesive coupled to the first adhesive and having a plurality of apertures extending through the second adhesive, each aperture exposing at least a portion of the first adhesive through the second adhesive,
      a first release member releasably coupled to the first side of the outer layer, and
      a second release member releasably coupled to the second adhesive; and
   a solution configured to decrease an adhesive strength of the first adhesive if applied to the first side of the outer layer.

10. The kit of claim 9, wherein the solution comprises alcohol.

11. The kit of claim 9, wherein the solution further comprises a local pain killer.

12. The kit of claim 9, wherein the solution is adapted to decrease a tackiness of the first adhesive between about 0% and about 70%.

13. The kit of claim 9, wherein the solution is adapted to decrease a tackiness of the first adhesive by about 50%.

14. The kit of claim 9, further comprising:
   the first release member having gripping portions; and
   the second release member having gripping portions.

15. A sealing system for use in treating a tissue site on a patient with reduced pressure, the sealing system comprising:
   an outer layer formed from a drape material and having a first side and a second side, wherein the outer layer is formed with a plurality of slits extending through the outer layer and having no drape material removed from the outer layer;
   a high-strength adhesive coupled to the second side of the outer layer, wherein the high-strength adhesive has a first side, a second side, and a tackiness;
   a sealing adhesive coupled to the high-strength adhesive and having a plurality of apertures extending through the sealing adhesive, each aperture exposing at least a portion of the high-strength adhesive through the sealing adhesive; and
   a switching solution, wherein when the switching solution is applied to the high-strength adhesive, the tackiness of the high-strength adhesive decreases.

16. The sealing system of claim 15, wherein the plurality of slits have an average effective diameter between about 0.05 mm and about 0.4 mm.

17. The sealing system of claim 15, wherein a surface area of the drape material removed to form the plurality of slits is between about 0.2% to about 13% of surface area of the outer layer.

18. The sealing system of claim 15, wherein the high-strength adhesive comprises an acrylic adhesive.

19. The sealing system of claim 15, wherein the high-strength adhesive further comprises expansion members that are configured to expand primarily perpendicularly to the second side of the outer layer when activated by the switching solution.

20. The sealing system of claim 15, wherein the switching solution comprises alcohol.

* * * * *